(12) United States Patent
Stucke et al.

(10) Patent No.: US 7,550,443 B2
(45) Date of Patent: Jun. 23, 2009

US007550443B2

(54) PROCESS AND SYSTEMS FOR BIOCOMPATIBLE SURFACES

(75) Inventors: Sean M. Stucke, Farmington, MN (US); Ralph A. Chappa, Prior Lake, MN (US); Joseph A. Chinn, Shakopee, MN (US)

(73) Assignee: SurModics, Inc., Eden Prairie, MN (US)

( * ) Notice: Subject to any disclaimer, the term of this patent is extended or adjusted under 35 U.S.C. 154(b) by 631 days.

(21) Appl. No.: 11/090,517

(22) Filed: Mar. 25, 2005

(65) Prior Publication Data

US 2005/0232970 A1 Oct. 20, 2005

Related U.S. Application Data

(60) Provisional application No. 60/556,634, filed on Mar. 26, 2004, provisional application No. 60/568,021, filed on May 3, 2004.

(51) Int. Cl.
*A61K 31/727* (2006.01)
*A61K 9/14* (2006.01)
*A61K 9/50* (2006.01)

(52) U.S. Cl. ............... 514/56; 424/484; 424/486; 424/499

(58) Field of Classification Search ............... 514/56; 424/484, 486, 499
See application file for complete search history.

(56) References Cited

U.S. PATENT DOCUMENTS

| | | | |
|---|---|---|---|
| 5,002,582 A | 3/1991 | Guire et al. | |
| 5,252,701 A | 10/1993 | Jarrett et al. | |
| 5,350,800 A | 9/1994 | Verhoeven et al. | |
| 5,414,075 A | 5/1995 | Swan et al. | |
| 5,443,458 A | 8/1995 | Eury | |
| 5,563,056 A * | 10/1996 | Swan et al. ............... 435/180 |
| 5,637,460 A | 6/1997 | Swan et al. | |
| 5,714,360 A | 2/1998 | Swan et al. | |
| 5,788,979 A | 8/1998 | Alt et al. | |
| 6,120,536 A | 9/2000 | Ding et al. | |
| 6,214,901 B1 | 4/2001 | Chudzik et al. | |
| 6,231,600 B1 | 5/2001 | Zhong | |
| 6,299,604 B1 | 10/2001 | Ragheb et al. | |
| 6,387,379 B1 | 5/2002 | Goldberg et al. | |
| 6,503,538 B1 | 1/2003 | Chu et al. | |
| 6,509,104 B2 | 1/2003 | Huang et al. | |
| 6,559,132 B1 | 5/2003 | Holmer et al. | |
| 6,599,558 B1 | 7/2003 | Al-Lamee et al. | |
| 6,600,010 B2 | 7/2003 | Mao et al. | |
| 6,620,194 B2 | 9/2003 | Ding et al. | |
| 6,656,206 B2 | 12/2003 | Corcoran et al. | |
| 6,669,980 B2 | 12/2003 | Hansen | |
| 6,669,994 B2 | 12/2003 | Swan et al. | |
| 6,702,850 B1 | 3/2004 | Byun et al. | |
| 6,713,119 B2 | 3/2004 | Hossainy et al. | |
| 6,759,054 B2 | 7/2004 | Chen et al. | |
| 6,790,228 B2 * | 9/2004 | Hossainy et al. ............ 623/1.46 |
| 2001/0007083 A1 | 7/2001 | Roorda | |
| 2001/0029351 A1 | 10/2001 | Falotico et al. | |
| 2002/0087123 A1 | 7/2002 | Hossainy et al. | |
| 2002/0188037 A1 | 12/2002 | Chudzik et al. | |
| 2003/0059631 A1 | 3/2003 | Al-Lamee | |
| 2003/0161938 A1 | 8/2003 | Johnson | |
| 2003/0165613 A1 | 9/2003 | Chappa et al. | |
| 2004/0005470 A1 | 1/2004 | Koulik | |
| 2004/0047911 A1 | 3/2004 | Lyu et al. | |
| 2005/0004663 A1 | 1/2005 | Llanos et al. | |
| 2005/0060028 A1 | 3/2005 | Horres et al. | |
| 2005/0244453 A1 | 11/2005 | Stucke et al. | |

FOREIGN PATENT DOCUMENTS

| | | |
|---|---|---|
| EP | 0923953 | 6/1999 |
| EP | 0950386 | 10/1999 |
| EP | 0568310 | 11/1999 |
| WO | WO98/36784 | 8/1998 |
| WO | WO99/64086 | 12/1999 |
| WO | WO03/030879 | 4/2003 |
| WO | WO03/105920 | 12/2003 |
| WO | WO2004/075943 | 10/2004 |

OTHER PUBLICATIONS

Grube et al. Six- and Twelve-Month Results From First Human Experience Using Everolimus-Eluting Stents With Bioabsorbable Polymer, Circulation 2004;109;2168-2171.*
Hietala et al. Biodegradation of the copolymeric polylactide Stent—long term followup in a rabbit aorta model, Journal of Vascular Research, 2001;38:361-369.*
Clapper, D.L, et al. (1995) *Mater. Technol.* 10:147-149.
Nakayama, Y, et al. (2002)*J Biomed Mater Res* 64A:52-61.

* cited by examiner

*Primary Examiner*—Raymond J Henley, III
(74) *Attorney, Agent, or Firm*—Kagan Binder, PLLC

(57) ABSTRACT

The invention provides methods and compositions for providing biocompatible surfaces to medical articles. In particular the invention provides biocompatible coatings with heparin activity that are able to release a bioactive agent, wherein the coatings are formed using biostable or biodegradable polymeric material and photoreactive groups.

17 Claims, 3 Drawing Sheets

PROCESS AND SYSTEMS FOR BIOCOMPATIBLE SURFACES

CROSS-REFERENCE TO RELATED APPLICATION

The present non-provisional Application claims the benefit of commonly owned provisional Application having Ser. No. 60/556,634, filed on Mar. 26, 2004, and entitled PROCESS AND SYSTEMS FOR BIOCOMPATIBLE SURFACES; and commonly owned provisional Application having Ser. No. 60/568,021, filed on May 3, 2004, and entitled COMPOSITION AND METHOD FOR PREPARING BIOCOMPATIBLE SURFACES; which Applications are incorporated herein by reference in their entirety.

FIELD OF THE INVENTION

The invention relates to preparation of biocompatible surfaces. More particularly, the invention relates to providing biocompatible surfaces by coupling biocompatible agent to a surface of a medical article.

BACKGROUND OF THE INVENTION

Recently, the use of drug-eluting stents (DES) in percutaneous coronary interventions has received much attention. DES are medical devices that present or release bioactive agent into their surroundings (for example, luminal walls or coronary arteries). Generally speaking, bioactive agent can be coupled to the surface of a medical device by surface modification, embedded and released from within polymer materials (matrix-type), or surrounded by and released through a carrier (reservoir-type). The polymer materials in such applications should optimally act as a biologically inert barrier and not induce further inflammation within the body. However, the molecular weight, porosity of the polymer, a greater percentage of coating exposed on the medical device, and the thickness of the polymer coating can contribute to adverse reactions to the medical device.

Improved compatibility with blood is a desired feature for a variety of medical devices that contact blood during clinical use. The materials used for manufacture of medical devices are not inherently compatible with blood and its components, and the response of blood to a foreign material can be aggressive, resulting in surface induced thrombus (clot) formation. This foreign body response can in turn impair or disable the function of the device and, most importantly, threaten patient health. It is often desirable to modify the surface of medical devices, such as DES, to provide a biocompatible surface, to minimize or avoid such adverse foreign body responses.

As used herein, a surface of a medical article is characterized as "biocompatible" if it is capable of functioning or existing in contact with biological fluid and/or tissue of a living organism with a net beneficial effect on the living organism. Long-term biocompatibility is desired for the purpose of reducing disturbance of a host organism. One approach to improved biocompatibility for medical device surfaces is to attach various biomolecules such as antithrombogenic agents, anti-restenotic agents, cell attachment proteins, growth factors, and the like, to the surface of the device. For example, antithrombogenic agents can reduce the generation of substances as part of the clotting cascade, antirestenotic agents can reduce generation of aggressive scar tissue growth around the device, while cell attachment proteins can contribute to the growth of a layer of endothelial cells around the device.

Several benefits can be provided by biocompatible medical device surfaces. For example, such surfaces can increase patient safety, improve device performance, reduce adherence of blood components, inhibit blood clotting, keep device surfaces free of cellular debris, and/or extend the useable lifetime of the device.

One biomolecule that has been utilized to improve biocompatibility of medical device surfaces is heparin. Heparin is a pharmaceutical that has been used clinically for decades as an intravenous anticoagulant to treat inherent clotting disorders and to prevent blood clot formation during surgery and interventional procedures. Heparin molecules are polysaccharides with a unique chemical structure that gives them specific biological activity. When heparin is immobilized onto the surface of a medical device material, it can improve the performance of the material when in contact with blood in several ways: 1) it can provide local catalytic activity to inhibit several enzymes critical to the formation of fibrin (which holds thrombi together); 2) it can reduce the adsorption of blood proteins, many of which lead to undesirable reactions on the device surface; and 3) it can reduce the adhesion and activation of platelets, which are a primary component of thrombus.

In addition to heparin, other biomolecules that can be provided on a medical device to improve biocompatibility include extracellular matrix (ECM) proteins or ECM peptides derived from these proteins. Surfaces modified with appropriate proteins or peptides are less likely to be recognized as foreign than the original device surface and will promote the attachment and overgrowth of specific desirable cell types.

The preparation of biocompatible surfaces, however, can be challenging. This is particularly the case when attempting to provide biocompatibility to devices that also have other properties, such as DES. Materials that are used to form these coating may not be inherently compatible with each other, thereby making it difficult to form a coating that is both biocompatible and that has drug-releasing properties.

In addition, treatments that are used to form coatings can in some cases damage the bioactive agent and therefore reduce the overall effectiveness of the coated article. This may be the case when irradiation is used to form all or part of the coating. Irradiation sources can be useful for activating components of a coating composition to form the coating, but can also lack the specificity and therefore cause degradation of the bioactive agent that is present in the coating.

Another problem relates to the release of bioactive agent, as some materials release the bioactive agent immediately upon contact with tissue; therefore the bioactive agent is not present for an amount of time sufficient to provide a beneficial effect.

SUMMARY OF THE INVENTION

The invention relates to methods and systems for providing biocompatible surfaces to medical devices.

In one aspect, the invention provides methods of coupling a biocompatible agent to a surface of a medical article, the methods including the following steps: (a) providing a polymeric material on a surface of a medical article, the polymeric material comprising one or more bioactive agents; and (b) providing biocompatible agent to the polymeric material under conditions sufficient to couple the biocompatible agent to the polymeric material, wherein coupling of the biocompatible agent with the polymeric material is accomplished by activating photoreactive groups provided by the polymeric material, the biocompatible agent, or both the polymeric material and the biocompatible material.

In other aspects, the invention provides methods of preparing a biocompatible surface on a medical article, the methods including steps of: (a) providing a medical article having a surface, at least a portion of the surface associated with a polymeric material comprising one or more bioactive agents; and (b) coupling biocompatible agent to the polymeric material to form a biocompatible surface on the medical article, wherein coupling of the biocompatible agent with the polymeric material is accomplished by activating photoreactive groups provided by the polymeric material, the biocompatible agent, or both the polymeric material and the biocompatible agent, and/or independent of these materials.

In some aspects of the invention, the polymeric material is a bio-stable polymer. The bio-stable polymer can be permeable to the bioactive agent, which can be released by diffusion through and out of the polymeric material.

The bio-stable polymer can be a bio-stable vinyl polymer. In some aspects of the invention, the biostable polymer is a vinyl alcohol polymer, for example a copolymer of a vinyl monomer, such as a vinyl alcohol, and a non-polar monomer such as ethylene; for example the copolymer can be poly(ethylene vinyl alcohol).

In other aspects the biostable polymer is a poly(alkyl (meth)acrylate), such as poly(butyl methacrylate). The poly (alkyl(meth)acrylate) can be in a mixture with one or more other polymers, for example, the mixture can be poly(butyl methacrylate) and poly(ethylene-co-vinyl acetate).

In some embodiments, the polymeric material on the surface of the medical article can be biodegradable. Exemplary biodegradable polymers include, for example, polylactic acid, polyglycolic acid, and other suitable biodegradable polymers.

The coating can also include other polymeric materials, such as Parylene™.

According to the invention, at least a portion of the surface of the medical article is coated with the polymeric material. In some embodiments, the entire surface of the medical article can be coated with the polymeric material. The amount of the surface area provided with the polymeric material can be determined according to such factors as the medical device to be utilized, the application of the device, the bioactive agent to be utilized with the polymeric material, and the like factors.

Preferably, the polymeric material includes one or more bioactive agents. In some embodiments, the polymeric material can include more than one bioactive agent, wherein each of the bioactive agents can be independently selected depending upon the desired therapeutic application of the invention. Some preferred bioactive agents of the present invention include sirolimus (rapamycin), analogs of rapamycin ("rapalogs"), tacrolimus, ABT-578, everolimus, paclitaxel, and taxane.

According to the invention, a biocompatible agent is coupled to the polymeric material to provide a biocompatible surface of the medical article. In some embodiments, more than one type of biocompatible agent is coupled with the polymeric material. The type and number of biocompatible agents provided in connection with the invention can be determined based upon the desired application and therapeutic effect of the invention.

In preferred aspects, the biocompatible agent of the biocompatible layer is a hydrophilic polymer having biocompatible properties, herein referred to as a "hydrophilic biocompatible polymer". Preferably, the hydrophilic polymer has hemocompatible properties, meaning that it promotes compatibility with blood components by minimizing events that may compromise the function of the device, such as thrombus formation near the coated surface.

A hydrophilic hemocompatible polymer can be a natural polymer, or can be derived from a natural polymer. The hydrophilic hemocompatible polymer can also include charged groups, such as sulfonate groups. In some aspects the hydrophilic polymer is a polysaccharide. According to the invention, particularly useful polysaccharides can be selected from mucopolysaccharides such as heparin, hyaluronic acid, chondroitin, keratan, and dermatan. In preferred embodiments the biocompatible polymer is heparin. In some preferred embodiments, the biocompatible polymer is selected from heparin, heparin derivatives, sodium heparin, and low molecular weight heparin. As used herein "heparin" is meant to encompass all forms of heparin, including derivatives and different molecular weight preparations of heparin.

It has been discovered that a bioactive agent releasing coating that has excellent heparin activity can be formed according to the inventive methods described herein. In determining the heparin activity, an assay can be performed and compared to results of an assay performed using heparin standards.

Therefore, in some aspects, the invention provides a medical article having a bioactive agent-releasing coating having heparin activity of 10 $mU/cm^2$ or greater. Bioactive agent-releasing coatings were also prepared having a heparin activity of 15 $mU/cm^2$ or greater, 20 $mU/cm^2$ or greater, 25 $mU/cm^2$ or greater, 30 $mU/cm^2$ or greater, 35 $mU/cm^2$ or greater, 40 $mU/cm^2$ or greater, 45 $mU/cm^2$ or greater, and 50 $mU/cm^2$ or greater. These coating can include a first coated layer comprising a bio-stable or biodegradable polymer and a bioactive agent, and a second coated layer that includes heparin and photoreactive groups.

In some embodiments, the biocompatible agent, such as heparin, includes one or more photoreactive groups, and coupling of the biocompatible agent to the polymeric material is accomplished by activating one or more of the photoreactive groups of the biocompatible agent. In other aspects of the invention, the polymeric material includes one or more photoreactive groups, and coupling of the biocompatible agent to the polymeric material is accomplished by activating one or more of the photoreactive groups of the polymeric material.

In some embodiments of the invention, a filter is utilized in connection with activation of the one or more photoreactive groups. In some embodiments, the one or more photoreactive groups are activated by providing light having a wavelength selected in a range to activate the photoreactive groups and used in conjunction with a filter to minimize inactivation of bioactive agent in the polymeric material. It has been found that use of the filtered irradiation methods described herein provide a bioactive agent releasing coating having excellent biocompatible properties while at the same time preventing significant loss of the bioactive agent by degradation.

Therefore, in some embodiments, a filter is utilized to form a bioactive agent-releasing biocompatible coating on the surface of a medical article. The biocompatible coating can have one or more coated layers and, in some aspects, have heparin activity. The coating includes a first coated layer comprising a polymer and a bioactive agent. The bioactive agent absorbs light maximally at less than about 300 nm, and typically in the range of 200 nm to 300 nm. The coating also includes second coated layer comprising a biocompatible agent, such as heparin, and photoreactive groups. The photoreactive groups maximally absorb light in a wavelength at about 320 nm and above, and preferably in the range of 330 nm to 340 nm. The coating can be formed by applying irradiation through a filter in an amount in the range of about 0.12 $J/cm^2$ about 0.96 $J/cm^2$ as measured at 335 nm. A more preferred range is about 0.12 $J/cm^2$ to about 0.72 $J/cm^2$. The filter that is used can be selected from the group consisting of ultra-violet cut-off filters, ultra-violet transmitting filters, band pass filters, and colored filters. Suitable band pass filters having a having a center wavelength in the range of about 380 nm to about 470 nm, and suitable UV cut-off filters have a cut-off transmittance in the range of about 320 nm and above, preferably in the range of about 320 nm to 330 nm.

In some aspects of the invention, auxiliary components can be added to improve formation of the biocompatible, bioactive agent releasing coating. The auxiliary component can be in mixture with the polymeric material, the bioactive agent, the biocompatible agent, or combinations of these. Optionally, the auxiliary component can be present in a separate coated layer on the surface of the article.

The auxiliary component can be selected from non-water soluble crosslinking agents, vinylpyrrolidone polymers, polyethylene glycol, polyethylene glycol sulfonates, fatty quaternary amines, fatty sulfonates, fatty acids, dextran, dextrin, and cyclodextrin. Preferably the auxiliary component has pendent photo-reactive groups. The auxiliary component can be used in conjunction with coatings that include biostable polymeric material or biodegradable polymeric material.

It has been discovered that the presence of the auxiliary component provides for formation of coatings, in particular biodegradable coatings, having excellent biocompatible properties, such as excellent heparin activity. Therefore in some aspects, the invention provides a medical article having a biodegradable coating with heparin activity, the coating comprising a biodegradable polymer, bioactive agent, heparin having pendent photo-reactive groups, and a component selected from the group of non-water soluble crosslinking agents, vinylpyrrolidone polymers, polyethylene glycol, polyethylene glycol sulfonates, fatty quaternary amines, fatty sulfonates, fatty acids, dextran, dextrin, and cyclodextrin, the component having pendent photo-reactive groups. Preferably, the auxiliary component is a non-water soluble crosslinking agents or a vinylpyrrolidone polymer having pendent photoreactive groups.

In some aspects, the auxiliary component is premixed with the biocompatible agent, such as heparin, prior to application on the polymeric material.

In other aspects, the coating can be formed by disposing a coating composition that includes the biodegradable polymer, heparin having pendent photo-reactive groups, and an auxiliary reagent having pendent photo-reactive groups. For example, a crosslinking reagent or a vinylpyrrolidone polymer can be combined with a polymeric material and the biocompatible agent prior to providing disposing the composition on the article. This composition can also include a bioactive agent that can be released as the coating degrades. A bioactive agent can also be present in another coated layer, for example a layer that includes a biodegradable polymer.

In yet other aspects, the inventive methods further include a step of providing a priming layer that includes the auxiliary component on the medical article prior to providing a composition that includes the biocompatible agent to the article. The priming polymer can be selected from photo-polyvinylpyrrolidone and other suitable auxiliary components, as described herein.

In another embodiment, the invention provides medical article having a biodegradable coating with heparin activity, the coating comprising a biodegradable polymer, a bioactive agent, heparin having pendent photo-reactive groups, and a component selected from the group of non-water soluble crosslinking agents, vinylpyrrolidone polymers, polyethylene glycol, polyethylene glycol sulfonates, fatty quaternary amines, fatty sulfonates, fatty acids, dextran, dextrin, and cyclodextrin, the component having pendent photo-reactive groups. In some embodiments, the coating can include two or more coated layers.

The component having photo-reactive groups can be present in a coated layer that is not a coated layer that includes the heparin having pendent photoreactive groups and the biodegradable polymer. In some cases, the biodegradable polymer is present in two or more coated layers. In other cases, the biodegradable polymer and the bioactive agent are both present in a coated layer. In yet other cases, the heparin comprising photoreactive groups, the biodegradable polymer, and the component having photo-reactive groups are present in a coated layer. In yet other cases, the heparin comprising photoreactive groups, the biodegradable polymer, the component having photo-reactive groups, and the bioactive agent are present in a coated layer.

Application of the reagents described herein to medical article can be accomplished utilizing any known application technique. For example, in some embodiments, a composition that includes the biocompatible agent is applied to the polymeric material by dip coating the medical article in the composition and activating the photoreactive groups while the medical article is dipped into the composition. In other illustrative embodiments, a composition that includes the biocompatible agent can be applied in admixture with a solvent. A composition that includes the biocompatible agent can be applied by spray coating the admixture of the biocompatible agent in a solvent. The solvent can be any suitable solvent, as described herein, for example, THF.

In some aspects, an outer coating ("topcoat") of biocompatible agent can be applied to the final, biocompatible agent-containing medical article. The outer coating can be provided on a portion of, or the entirety of, the medical article surface.

In still further aspects, the invention provides a medical article that includes: substrate; polymeric material disposed on the substrate, the polymeric material comprising bioactive agent; and biocompatible reagent coupled to the polymeric material via one or more photoreactive groups that are provided by the polymeric material, the biocompatible reagent, or both the polymeric material and the biocompatible reagent. In some embodiments, the medical article can further include a crosslinking agent coupled to the polymeric material and the biocompatible reagent. Optionally, the medical article can include a second biocompatible reagent coupled to the coupled polymeric material-biocompatible reagent. The biocompatible reagent and the second biocompatible reagent can be the same or different, as desired.

The invention will now be described in more detail.

DETAILED DESCRIPTION

Figure 1:
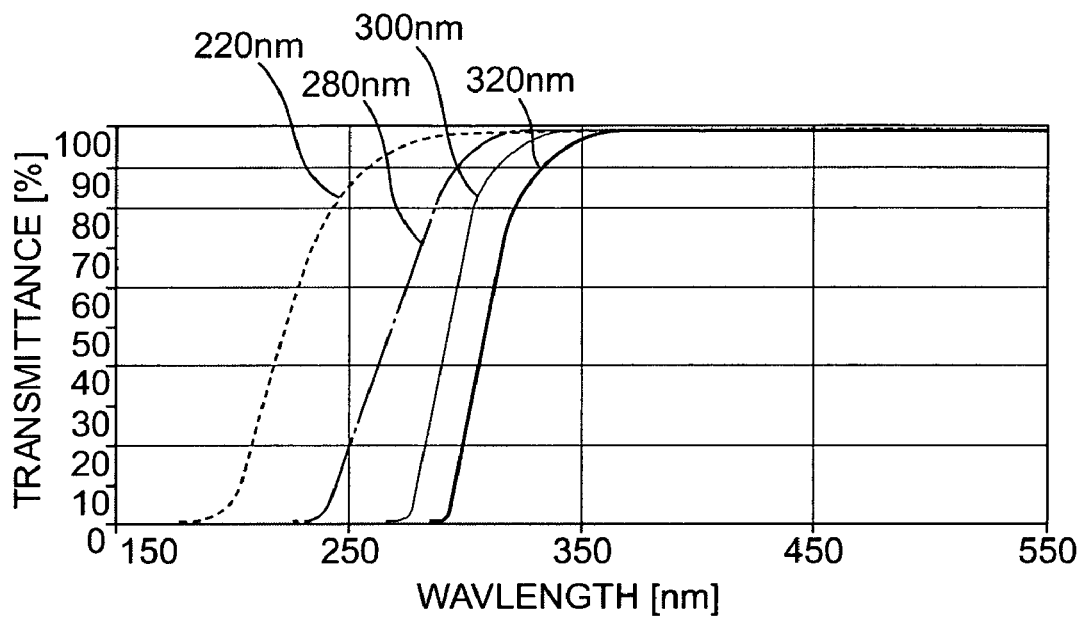
FIG. 1 is a graph of percent transmittance over a spectrum of wavelengths for various ultra-violet cutoff filters.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The present invention is directed to methods for preparing a biocompatible surface on a medical article. The biocompatible surface thus enhances the ability of the medical article to function or exist in contact with biological fluid and/or tissue of a living organism with a net beneficial effect on the living organism. In preferred embodiments, the biocompatible surface can provide one or more advantages, such as increased patient safety, improved device performance, reduced adherence of unwanted blood components, inhibition of blood clotting, maintenance of device surfaces free of cellular debris, and/or extension of the useable lifetime of the device.

The methods described herein are particularly suitable for preparing a biocompatible surface on a medical article that includes a polymeric material disposed on the surface, the polymeric material including one or more bioactive agents. The presence of one or more bioactive agents in the polymeric material on the surface of the medical article can render the device surface sensitive to irradiation with light, since certain wavelengths can inactivate bioactive agents.

The invention relates to methods for providing a biocompatible surface to an implantable medical article. The implantable medical article can be, for example, a stent or a synthetic graft having a structure adapted for the introduction into a patient. The device is preferably coated with a polymeric material that can include one or more bioactive agents for delivery of a drug or pharmaceutical substance to tissues adjacent the site of implantation. To facilitate discussion of the invention, use of the invention to provide a biocompatible coating to a stent having a drug-containing polymeric matrix on its surface will be discussed. The polymeric matrix can either be biodegradable or biostable. Some stents having biostable matrices with a bioactive agent are also referred to as a drug-eluting stents, or "DES". Use of the inventive concepts in connection with DES has been chosen because these devices are designed to reside in the body for extended periods of time, thus increasing risk of adverse body reactions to the device. Further, in terms of lowering the risk while providing a superior device, the advantages of this invention can be clearly presented. However, it is understood that the methods disclosed are applicable to any medical articles where attachment of a biocompatible agent are desirable, and are not limited to the particular medical article surfaces described herein.

The invention provides methods of providing biocompatible surfaces to medical devices that carry a polymeric material having bioactive agents associated therewith. The invention can be utilized in connection with medical devices having a variety of biomaterial surfaces. Preferred biomaterials include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, and vinylidene difluoride. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polylactic acid, polyglycolic acid, polydimethylsiloxanes, and polyetherketone.

Certain natural materials are also suitable biomaterials, including human tissue such as bone, cartilage, skin and teeth; and other organic materials such as wood, cellulose, compressed carbon, and rubber. Other suitable biomaterials include metals and ceramics. The metals include, but are not limited to, titanium, Nitinol, stainless steel, tantalum, and cobalt chromium. A second class of metals includes the noble metals such as gold, silver, copper, and platinum uridium. Alloys of metals are suitable for biomaterials as well. The ceramics include, but are not limited to, silicon nitride, silicon carbide, zirconia, and alumina, as well as glass, silica, and sapphire.

Combinations of ceramics and metals are another class of biomaterials. Another class of biomaterials is fibrous or porous in nature. The surface of such biomaterials can be pretreated (for example, with a Parylene™ coating composition) in order to alter the surface properties of the biomaterial, when desired.

Biomaterials can be used to fabricate a variety of implantable devices. The medical device can be any device that is introduced temporarily or permanently into a mammal for the prophylaxis or treatment of a medical condition. These devices include any that are introduced subcutaneously, percutaneously or surgically to rest within an organ, tissue, or lumen of an organ, such as arteries, veins, ventricles or atria of the heart.

Compositions of this invention can be used to coat the surface of a variety of implantable devices, for example: drug-delivering vascular stents; other vascular devices (e.g., grafts, catheters, valves, artificial hearts, heart assist devices); implantable defibrillators; blood oxygenator devices; surgical devices; tissue-related materials; membranes; cell culture devices; chromatographic support materials; biosensors; shunts for hydrocephalus; wound management devices; endoscopic devices; infection control devices; orthopedic devices; dental devices, urological devices; colostomy bag attachment devices; ophthalmic devices; glaucoma drain shunts; synthetic prostheses; intraocular lenses; respiratory, peripheral cardiovascular, spinal, neurological, dental, ear/nose/throat (e.g., ear drainage tubes); renal devices; and dialysis (e.g., tubing, membranes, grafts).

Examples of useful devices include self-expanding stents (e.g., made from nitinol), balloon-expanded stents (e.g., prepared from stainless steel), degradable coronary stents, non-degradable coronary stents, peripheral coronary stents, urinary catheters (e.g., surface-coated with antimicrobial agents), penile implants, sphincter devices, urethral devices, bladder devices, renal devices, vascular implants and grafts, intravenous catheters (e.g., treated with antithrombotic agents), small diameter grafts, artificial lung catheters, electrophysiology catheters, anastomosis devices, vertebral disks, bone pins, suture anchors, hemostatic barriers, clamps, surgical staples/sutures/screws/plates/clips, atrial septal defect closures, electro-stimulation leads for cardiac rhythm management (e.g., pacer leads), glucose sensors (long-term and short-term), blood pressure and stent graft catheters, blood oxygenator tubing, blood oxygenator membranes, blood bags, birth control devices, breast implants, ); benign prostatic hyperplasia and prostate cancer implants, bone repair/augmentation devices, breast implants, cartilage repair devices, orthopedic joint implants, orthopedic fracture repairs, tissue adhesives, tissue sealants, tissue scaffolds, CSF shunts, dental implants, dental fracture repair devices, implanted drug infusion tubes, intravitreal drug delivery devices, nerve regeneration conduits, oncological implants, electrostimulation leads, pain management implants, spinal/orthopedic repair devices, wound dressings, embolic protection filters, abdominal aortic aneurysm grafts, heart valves (e.g., mechanical, polymeric, tissue, percutaneous, carbon, sewing cuff), valve annuloplasty devices, mitral valve repair devices, vascular intervention devices, left ventricle assist devices, neuro aneurysm treatment coils, neurological catheters, left atrial appendage filters, central venous access catheters, hemodialysis devices, catheter cuff, anastomotic closures, vascular access catheters, cardiac sensors, uterine bleeding patches, urological catheters/stents/implants, in vitro diagnostics, aneurysm exclusion devices, neuropatches, Vena cava filters, urinary dialators, endoscopic surgical tissue extractors, atherectomy catheters, clot extraction catheters, PTA catheters, PTCA catheters, stylets (vascular and non-vascular), coronary guidewires, drug infusion catheters, esophageal stents, circulatory support systems, angiographic catheters, transition sheaths and dialators, coronary and peripheral guidewires, hemodialysis catheters, neurovascular balloon catheters, tympanostomy vent tubes, cerebro-spinal fluid shunts, defibrillator leads, percutaneous closure devices, drainage tubes, thoracic cavity suction drainage catheters, electrophysiology catheters, stroke therapy catheters, abscess drainage catheters, biliary drainage products, dialysis catheters, central venous access catheters; and parental feeding catheters.

The compositions are particularly useful for those devices that will come in contact with aqueous systems, such as bodily fluids. Such devices are coated with a coating composition adapted to release bioactive agent in a prolonged and controlled manner, generally beginning with the initial contact between the device surface and its aqueous environment. It is important to note that the local delivery of combinations of bioactive agents may be utilized to treat a wide variety of conditions utilizing any number of medical devices, or to enhance the function and/or life of the device. Essentially, any type of medical device may be coated in some fashion with one or more bioactive agents that enhances treatment over use of the singular use of the device or bioactive agent.

According to the invention, the biocompatible agent is utilized to provide a biocompatible surface to a medical device. The solid surface that is rendered biocompatible is desirably of a synthetic or natural material that is insoluble in physiological fluids. The surface can be one or more surfaces of devices intended to function in contact with tissue and/or fluids of living organisms.

According to some embodiments of the invention, a coating of a polymeric material is provided on the surface of the medical article. The polymers can be bio-stable or biodegradable, organic or inorganic, and synthetic or naturally-occurring substances. The polymeric material can be selected from a variety of polymeric materials. Preferably, the polymeric material is selected to incorporate a desirable amount of the bioactive agent, and to either retain the bioactive agent so that it is sufficiently presented to the surrounding physiological environment, or to release the bioactive agent to provide a desired elution profile. For example, bio-stable polymers can be permeable to the bioactive agent, which can be released by diffusion through and out of the polymeric material.

In some aspects of the invention, the bio-stable polymeric material is a bio-stable vinyl polymer. For example, the polymeric material can be a vinyl polymer that includes vinyl alcohol monomeric units. In some aspects, the polymeric material is a copolymer of a vinyl monomer, such as a vinyl alcohol, and a non-polar monomer such as ethylene vinyl alcohol copolymer, also know as EVOH or EVAL. Particularly useful ethylene vinyl alcohol copolymers can be dissolved in IPA-water mixtures. Ethylene vinyl alcohol copolymer coatings that include a bioactive agent can be formed on the surface of a medical article in accordance with the methods described in U.S. Pat. No. 6,759,054. Preferred ethylene vinyl alcohol copolymers have an ethylene molar content of about 27% to about 29%. Ethylene vinyl alcohol copolymers are commercially available from various sources including, for example, Soarus L.L.C. (Arlington Heights, Ill.) and Evalca (Arlington Heights, Ill.). Other monomers, for example, stryenes, propylene, and the like, can be added in small amounts (for example, less than about 5%) for the preparation of an ethylene vinyl alcohol copolymer.

In another embodiment, the polymeric material comprises a composition as described in U.S. Pat. No. 6,214,901 (Chudzik et al.) and U.S. Publication No. 2002/0188037 A1 (Chudzik et al.) (each commonly assigned to the assignee of the present invention). As described therein, the composition comprises a plurality of polymers, including a first polymer component and a second polymer component. The polymer components are adapted to be mixed to provide a mixture that exhibits an optimal combination of physical characteristics (such as adherence, durability, flexibility) and bioactive release characteristics as compared to the polymers when used alone or in admixture with other polymers previously known.

Examples of suitable first polymers according to this particular embodiment include poly(alkyl(meth)acrylates), and in particular, those with alkyl chain lengths from 2 to 8 carbons, and with molecular weights from 50 kilodaltons (kD) to 900 kD. An example of a preferred first polymer is poly n-butylmethacrylate. Such polymers are available commercially, for example, from Aldrich, with molecular weights ranging from about 200 Daltons to about 320,000 Daltons, and with varying inherent viscosity, solubility, and form (for example, as crystals or powder).

Second polymers according to this embodiment provide an optimal combination of similar properties, and particularly when used in admixture with the first polymer component. Examples of suitable second polymers are available commercially and include poly(ethylene-co-vinyl acetate) having vinyl acetate concentrations in the range of about 1-% to about 50%, in the form of beads, pellets, granules, and the like.

In a preferred embodiment, the composition comprises at least one poly(alkyl(meth)acrylate), as a first polymeric component, and poly(ethylene-co-vinyl acetate) as a second polymeric component. Preferably, the polymer mixture includes mixtures of poly(butyl(meth)acrylate) (pBMA) and poly(ethylene-co-vinyl acetate) (pEVA). This mixture of polymers has proven useful with absolute polymer concentrations (total combined concentrations of both polymers in the composition) in the range of about 0.25 to about 70% (by weight). It has furthermore proven effective with individual polymer concentrations in the coating solution in the range of about 0.05 to about 70% (by weight). In one preferred embodiment, the polymer mixture includes poly(n-butylmethacrylate) with a molecular weight in the range of about 100 kD to 900 kD and a pEVA copolymer with a vinyl acetate content in the range of about 24 to 36% (by weight). In another preferred embodiment, the polymer mixture includes poly(n-butylmethacrylate) with a molecular weight in the range of about 200 kD to 400 kD and a pEVA copolymer with a vinyl acetate content in the range of about 30 to 34% (by weight). According to these embodiments, the concentration of the bioactive agent or agents dissolved or suspended in the coating mixture can be in the range of about 0.01 to 90%, by weight, based on the weight of the final coating composition.

Other useful mixtures of polymers that can be included in the coating composition are described in commonly owned U.S. patent application entitled, "COATING COMPOSITIONS FOR BIOACTIVE AGENTS," U.S. Provisional Patent Application No. 60/559,821, filed Apr. 6, 2004). These blends includes a first polymer and a second polymer. The first polymer can be selected from the group consisting of (i) poly(alkylene-co-alkyl(meth)acrylates, (ii) ethylene copolymers with other alkylenes, (iii) polybutenes, (iv) diolefin derived non-aromatic polymers and copolymers, (v) aromatic group-containing copolymers, and (vi) epichlorohydrin-containing polymers. A second polymer can be selected from the group consisting of poly(alkyl (meth)acrylates) and poly(aromatic(meth)acrylates).

Other useful mixtures of polymers that can be included in the coating are described in U.S. Publication No. 2004/0047911. This publication describes polymer blends that include poly(ethylene-co-methacrylate) and a polymer selected from the group consisting of a poly(vinyl alkylate), a poly(vinyl alkyl ether), a poly(vinyl acetal), a poly(alkyl and/or aryl methacrylate) or a poly(alkyl and/or aryl acrylate); not including pEVA.

The polymeric material can also be a styrene copolymer, such as poly(styrene-isobutylene-styrene); the preparation of medical devices having such coatings that include poly(styrene-isobutylene-styrene) is described in, for example, U.S. Pat. No. 6,669,980.

Other bio-stable polymeric materials include, but are not limited to, polymers of polyurethanes, polyethylenes, polyethylene teraphthalates, ethylene vinyl acetates, silicones and polyethylene oxide.

As used herein, biodegradable polymers are capable of being broken down by various enzymes, such as those in the normal functioning of the human body and living organisms (such as bacteria) and/or in water environments (simple hydrolysis). Once broken down, these polymers are gradually absorbed or eliminated by the body.

Examples of classes of synthetic polymers that have been studied as biodegradable materials include polyesters, polyamides, polyurethanes, polyorthoesters, polycaprolactone (PCL), polyiminocarbonates, aliphatic carbonates, polyphosphazenes, polyanhydrides, and copolymers thereof. Specific examples of biodegradable materials that can be used in connection with implantable medical devices include polylactide, polygylcolide, polydioxanone, poly(lactide-co-glycolide), poly(glycolide-co-polydioxanone), polyanhydrides, poly(glycolide-co-trimethylene carbonate), and poly(glycolide-co-caprolactone). Blends of these polymers with other biodegradable polymers can also be used. Typically, release of a bioactive agent occurs as these polymers dissolve or degrade in situ.

Biodegradable polyetherester copolymers can be used. Generally speaking, the polyetherester copolymers are amphiphilic block copolymers that include hydrophilic (for example, a polyalkylene glycol, such as polyethylene glycol) and hydrophobic blocks (for example, polyethylene terephthalate). Examples of block copolymers include poly(ethylene glycol)-based and poly(butylene terephthalate)-based blocks (PEG/PBT polymer). Examples of these types of multiblock copolymers are described in, for example, U.S. Pat. No. 5,980,948. PEG/PBT polymers are commercially available from Octoplus BV, under the trade designation PolyActive™.

Biodegradable copolymers having a biodegradable, segmented molecular architecture that includes at least two different ester linkages can also be used. The biodegradable polymers can be block copolymers (of the AB or ABA type) or segmented (also known as multiblock or random-block) copolymers of the $(AB)_n$ type. These copolymers are formed in a two (or more) stage ring opening copolymerization using two (or more) cyclic ester monomers that form linkages in the copolymer with greatly different susceptibilities to transesterification. Examples of these polymers are described in, for example, in U.S. Pat. No. 5,252,701 (Jarrett et al., "Segmented Absorbable Copolymer").

Other suitable biodegradable polymer materials include biodegradable terephthalate copolymers that include a phosphorus-containing linkage. Polymers having phosphoester linkages, called poly(phosphates), poly(phosphonates) and poly(phosphites), are known. See, for example, Penczek et al., Handbook of Polymer Synthesis, Chapter 17: "Phosphorus-Containing Polymers," 1077-1132 (Hans R. Kricheldorf ed., 1992), as well as U.S. Pat. Nos. 6,153,212, 6,485,737, 6,322,797, 6,600,010, 6,419,709. Biodegradable terephthalate polyesters can also be used that include a phosphoester linkage that is a phosphite. Suitable terephthalate polyester-polyphosphite copolymers are described, for example, in U.S. Pat. No. 6,419,709 (Mao et al., "Biodegradable Terephthalate Polyester-Poly(Phosphite) Compositions, Articles, and Methods of Using the Same). Biodegradable terephthalate polyester can also be used that include a phosphoester linkage that is a phosphonate. Suitable terephthalate polyester-poly(phosphonate) copolymers are described, for example, in U.S. Pat. Nos. 6,485,737 and 6,153,212 (Mao et al., "Biodegradable Terephthalate Polyester-Poly(Phosphonate) Compositions, Articles and Methods of Using the Same). Biodegradable terephthalate polyesters can be used that include a phosphoester linkage that is a phosphate. Suitable terephthalate polyester-poly(phosphate) copolymers are described, for example, in U.S. Pat. Nos. 6,322,797 and 6,600,010 (Mao et al., "Biodegradable Terephthalate Polyester-Poly(Phosphate) Polymers, Compositions, Articles, and Methods for Making and Using the Same).

Biodegradable polyhydric alcohol esters can also be used (See U.S. Pat. No. 6,592,895). This patent describes biodegradable star-shaped polymers that are made by esterifying polyhydric alcohols to provide acyl moieties originating from aliphatic homopolymer or copolymer polyesters. The biodegradable polymer can be a three-dimensional crosslinked polymer network containing hydrophobic and hydrophilic components which forms a hydrogel with a crosslinked polymer structure, such as that described in U.S. Pat. No. 6,583, 219. The hydrophobic component is a hydrophobic macromer with unsaturated group terminated ends, and the hydrophilic polymer is a polysaccharide containing hydroxy groups that are reacted with unsaturated group introducing compounds. The components are convertible into a one-phase crosslinked polymer network structure by free radical polymerization. In yet further embodiments, the biodegradable polymer can comprise a polymer based upon α-amino acids (such as elastomeric copolyester amides or copolyester urethanes, as described in U.S. Pat. No. 6,503,538).

As used herein, a hydrogel is a polymeric material that exhibits the ability to swell in water and retain a significant portion of water within its structure without dissolving. When the polymer comprises a hydrogel, the hydrogel can entrap a bioactive agent or physically encapsulate the bioactive agent.

Physical encapsulation can be achieved by swelling the hydrogel and introducing the bioactive agent to the hydrogel matrix. Generally, higher swelling ratios of hydrogel give faster drug release. In still further embodiments, the bioactive agent can be incorporated into the hydrogel by forming covalent bonds between the polymer forming the hydrogel and the bioactive agents. In still further embodiments, bioactive agents can be incorporated into the hydrogel by mixing the polymer components used to form the hydrogel with the bioactive agents, and polymerizing the mixture, thereby incorporating the bioactive agents during free radical polymerization.

In some embodiments, the polymeric material comprises Parylene™ or a Parylene™ derivative. "Parylene™" is both a generic name for a known group of polymers based on p-xylylene and made by vapor phase polymerization, and a name for the unsubstituted form of the polymer; the latter usage is employed herein. More particularly, Parylene™ or a Parylene™ derivative is created by first heating p-xylylene or a suitable derivative at an appropriate temperature (for example, at about 100-150° C.) to produce the cyclic dimer di-p-xylylene (or a derivative thereof). The resultant solid can be separated in pure form, and then cracked and pyrolyzed at an appropriate temperature (for example, at about 690° C.) to produce a monomer vapor of p-xylylene (or derivative); the monomer vapor is cooled to a suitable temperature (for example, below 30° C.) and allowed to condense on the desired object, for example, on the surface of the medical device.

As indicated, Parylene™ and Parylene™ derivative coatings applicable by vapor deposition are known for a variety of biomedical uses, and are commercially available from or through a variety of sources, including Specialty Coating Systems (100 Deposition Drive, Clear Lake, Wis. 54005), Para Tech Coating, Inc. (35 Argonaut, Aliso Viejo, Calif. 92656) and Advanced Surface Technology, Inc. (9 Linnel Circle, Billerica, Mass. 01821-3902).

In some embodiments, the polymeric material can include one or more bioactive agents. The bioactive agent can be release by particle dissolution or diffusion when bio-stable matrices are used, or during polymer breakdown when absorbed into a biodegradable substance. Alternatively, one or more bioactive agents can be presented to the physiological environment without being released from the polymeric material. For example, the bioactive agent(s) can be covalently coupled to the polymeric material so that the agent(s) are not released from the polymeric material into the physiological environment.

The coating composition on the medical device can comprise one or more bioactive agents incorporated into a polymeric material so that the bioactive agent is presented to or released locally into the adjacent or surrounding tissue. If released, the bioactive agent is preferably released in a slow or controlled-release manner, to provide the desired elution profile to achieve the therapeutic effect. The release of the bioactive agent in a controlled release manner allows for smaller amounts of the bioactive agent to be released for a long period of time in a zero order elution profile manner. The release kinetics of the bioactive agent can further depend upon such factors as the hydrophobicity of the bioactive agent (for example, a more hydrophobic bioactive agent is typically exhibits a slower the rate of release from the polymeric material). Alternatively, hydrophilic bioactive agents can be released from the polymeric material at a faster rate. Therefore, the polymeric composition can be altered according to the bioactive agent to be delivered in order to maintain the desired concentration of bioactive agent required at the treatment site for a longer period of time. As will be apparent upon review of this disclosure, the medical device can therefore provide a long-term effect of the bioactive agent at the treatment site that is more efficient in preventing restenosis and reduces side effects of the bioactive agents utilized.

For purposes of the description herein, reference will be made to "bioactive agent," but it is understood that the use of the singular term does not limit the application of bioactive agents contemplated, and any number of bioactive agents can be provided using the teaching herein. As used herein, "bioactive agent" refers to an agent that affects physiology of biological tissue. Bioactive agents useful according to the invention include virtually any substance that possesses desirable therapeutic characteristics for application to the implantation site.

The word "bioactive agent," as used herein, will refer to a wide range of biologically active materials or drugs that can be incorporated into a coating composition of the present invention. The bioactive agent(s) to be incorporated preferably do not chemically interact with the coating composition during fabrication or during the bioactive agent release process.

The term "bioactive agent," in turn, will refer to a peptide, protein, carbohydrate, nucleic acid, lipid, polysaccharide or combinations thereof, or synthetic inorganic or organic molecule, that causes a biological effect when administered in vivo to an animal, including but not limited to birds and mammals, including humans. Nonlimiting examples are antigens, enzymes, hormones, receptors, peptides, and gene therapy agents. Examples of suitable gene therapy agents include a) therapeutic nucleic acids, including antisense DNA and antisense RNA, and b) nucleic acids encoding therapeutic gene products, including plasmid DNA and viral fragments, along with associated promoters and excipients. Examples of other molecules that can be incorporated include nucleosides, nucleotides, antisense, vitamins, minerals, and steroids.

Coating compositions prepared according to this process can be used to deliver drugs such as nonsteroidal anti-inflammatory compounds, anesthetics, chemotherapeutic agents, immunotoxins, immunosuppressive agents, steroids, antibiotics, antivirals, antifungals, steroidal antiinflammatories, and anticoagulants. For example, hydrophobic drugs such as lidocaine or tetracaine can be included in the coating and are released over several hours.

Classes of medicaments which can be incorporated into coatings of this invention include, but are not limited to, anti-AIDS substances, anti-cancer substances, antibiotics, anti-viral substances, enzyme inhibitors, neurotoxins, opioids, hypnotics, antihistamines, immunosuppressants (e.g., cyclosporine), tranquilizers, anti-convulsants, muscle relaxants and anti-Parkinson substances, anti-spasmodics and muscle contractants, miotics and anti-cholinergics, immunosuppressants (e.g. cyclosporine), anti-glaucoma solutes, anti-parasite and/or anti-protozoal solutes, anti-hypertensives, analgesics, anti-pyretics and anti-inflammatory agents (such as NSAIDs), local anesthetics, ophthalmics, prostaglandins, anti-depressants, anti-psychotic substances, anti-emetics, imaging agents, specific targeting agents, neurotransmitters, proteins, and cell response modifiers. A more complete listing of classes of medicaments may be found in the Pharmazeutische Wirkstoffe, ed. A. Von Kleemann and J. Engel, Georg Thieme Verlag, Stuttgart/New York, 1987, incorporated herein by reference.

Antibiotics are art recognized and are substances which inhibit the growth of or kill microorganisms. Antibiotics can be produced synthetically or by microorganisms. Examples of antibiotics include penicillin, tetracycline, chloramphenicol, minocycline, doxycycline, vancomycin, bacitracin, kanamycin, neomycin, gentamycin, erythromycin, and cephalosporins geldanamycin, and analogs thereof. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone.

Antiseptics are recognized as substances that prevent or arrest the growth or action of microorganisms, generally in a nonspecific fashion, e.g., either by inhibiting their activity or destroying them. Examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

Anti-viral agents are substances capable of destroying or suppressing the replication of viruses. Examples of anti-viral agents include α-methyl-P-adamantane methylamine, hydroxy-ethoxymethylguanine, adamantanamine, 5-iodo-2'-deoxyuridine, trifluorothymidine, interferon, and adenine arabinoside.

Enzyme inhibitors are substances that inhibit an enzymatic reaction. Examples of enzyme inhibitors include edrophonium chloride, N-methylphysostigmine, neostigmine bromide, physostigmine sulfate, tacrine HCl, tacrine, 1-hydroxy-maleate, iodotubercidin, p-bromotetramisole, 10-(α-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, N-monomethyl-L-arginine acetate, carbidopa, 3-hydroxybenzylhydrazine HCl, hydralazine HCl, clorgyline HCl, deprenyl HCl, L(−), deprenyl HCl, D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthine, papaverine HCl, indomethacin, 2-cyclooctyl-2-hydroxyethylamine hydrochloride, 2,3-dichloro-α-methylbenzylamine (DCMB), 8,9-dichloro-2,3,4,5-tetrahydro-1H-2-benzazepine hydrochloride, p-aminoglutethimide, p-aminoglutethimide tartrate, R(+), p-aminoglutethimide tartrate, S(−), 3-iodotyrosine, alpha-methyltyrosine, L(−), alpha-methyltyrosine, D L(−), cetazolamide, dichlorphenamide, 6-hydroxy-2-benzothiazolesulfonamide, and allopurinol.

Anti-pyretics are substances capable of relieving or reducing fever. Anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide. Local anesthetics are substances which have an anesthetic effect in a localized region. Examples of such anesthetics include procaine, lidocaine, tetracaine and dibucaine.

Imaging agents are agents capable of imaging a desired site, e.g., tumor, in vivo. Examples of imaging agents include substances having a label which is detectable in vivo, e.g., antibodies attached to fluorescent labels. The term antibody includes whole antibodies or fragments thereof.

Cell response modifiers are chemotactic factors such as platelet-derived growth factor (pDGF). Other chemotactic factors include neutrophil-activating protein, monocyte chemoattractant protein, macrophage-inflammatory protein, SIS (small inducible secreted), platelet factor, platelet basic protein, melanoma growth stimulating activity, epidermal growth factor, transforming growth factor (alpha), fibroblast growth factor, platelet-derived endothelial cell growth factor, insulin-like growth factor, nerve growth factor, and bone growth/cartilage-inducing factor (alpha and beta). Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, activin, and DNA that encodes for the production of any of these proteins.

Additives such as inorganic salts, BSA (bovine serum albumin), and inert organic compounds can be used to alter the profile of bioactive agent release, as known to those skilled in the art.

The bioactive (e.g., pharmaceutical) agents useful in the present invention include virtually any therapeutic substance that possesses desirable therapeutic characteristics for application to the implant site. These agents include: thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives (including antiangiogenesis agents), anticancer chemotherapeutic agents, anti-inflammatory steroid or non-steroidal anti-inflammatory agents, immunosuppressive agents, growth hormone antagonists, growth factors, dopamine agonists, radiotherapeutic agents, peptides, proteins, enzymes, extracellular matrix components, ACE inhibitors, free radical scavengers, chelators, antioxidants, anti polymerases, antiviral agents, photodynamic therapy agents, gene therapy agents, and statins (such as lovastatin, pravastatin, simvastatin, fluvastatin, atorvastatin, cerivastatin, rousvastatin, and superstatin)

Other examples of suitable bioactive agents include sirolimus (rapamycin), analogs of rapamycin ("rapalogs"), tacrolimus, ABT-578 from Abbott, everolimus, paclitaxel, taxane, dexamethasone, betamethasone, paclitaxel, vinblastine, vincristine, vinorelbine, poside, teniposide, dactinomycin (actinomycin D), daunorubicin, doxorubicin, idarubicin, anthracyclines, mitoxantrone, bleomycins, plicamycin (mithramycin), mitomycin, mechlorethamine, cyclophosphamide and its analogs, melphalan, chlorambucil, ethylenimines and methylmelamines, alkyl sulfonates-busulfan, nirtosoureas, carmustine (BCNU) and analogs, streptozocin, trazenes-dacarbazinine, methotrexate, fluorouracil, floxuridine, cytarabine, mercaptopurine, thioguanine, pentostatin, 2-chlorodeoxyadenosine, cisplatin, carboplatin, procarbazine, hydroxyurea, mitotane, aminoglutethimide, estrogen, heparin, synthetic heparin salts, tissue plasminogen activator, streptokinase, urokinase, aspirin, dipyridamole, ticlopidine, clopidogrel, abciximab, breveldin, cortisol, cortisone, fludrocortisone, prednisone, prednisolone, 6U-methylprednisolone, triamcinolone, aspirin, acetaminophen, indomethacin, sulindac, etodalac, tolmetin, diclofenac, ketorolac, ibuprofen and derivatives, mefenamic acid, meclofenamic acid, piroxicam, tenoxicam, phenylbutazone, oxyphenthatrazone, nabumetone, auranofin, aurothioglucose, gold sodium thiomalate, cyclosporine, tacrolimus (FK-506), azathioprine, mycophenolate mofetil, vascular endothelial growth factor (VEGF), fibroblast growth factor (FGF); angiotensin receptor blocker;

nitric oxide donors; anti-sense oligionucleotides and combinations thereof; cell cycle inhibitors, mTOR inhibitors, and growth factor signal transduction kinase inhibitors.

A comprehensive listing of bioactive agents can be found in *The Merck Index*, Thirteenth Edition, Merck & Co. (2001). Bioactive agents are commercially available from Sigma Aldrich Fine Chemicals, Milwaukee, Wisc.

The concentration of the bioactive agent or agents dissolved or suspended in the coating mixture can range from about 0.01 to about 90 percent, by weight, based on the weight of the final coated composition.

The particular bioactive agent, or combination of bioactive agents, can be selected depending upon one or more of the following factors: the application of the controlled delivery device, the medical condition to be treated, the anticipated duration of treatment, characteristics of the implantation site, the number and type of bioactive agents to be utilized, and the like.

As indicated, in some embodiments, a coated composition or coated layer can include the biodegradable polymer and one or more bioactive agents. Optionally, a coated composition or coated layer can include the biodegradable polymer and other components described herein. For example, a composition can be prepared that includes the biodegradable polymer along with the biocompatible agent. The composition can be used to form a biodegradable coatings in which the biocompatible agent can be made continuously available from the surface of the coating as the biodegradable polymer erodes from the surface of the article. In some aspects, a bioactive agent is included, which can provide release of the bioactive agent and continuous biocompatibility as the coating degrades. In a preferred embodiment, the biodegradable coating also includes an auxiliary component that can improve formation of the biodegradable coating. Preferred auxiliary components include polyvinylpyrrolidone and non-water soluble crosslinking agents, wherein these components also include pendent photoreactive groups. The auxiliary component can be present in mixture with the biodegradable polymer, or can be present in a different coated layer.

In order to provide a preferred coating, a coating composition is prepared to include a solvent, a combination of complementary polymers dissolved in the solvent, and the bioactive agent(s) dissolved or dispersed in the polymer/solvent mixture. The solvent is preferably one in which the polymers form a homogeneous solution. The pharmaceutical agent itself may either be soluble in the solvent or form a dispersion throughout the solvent. Suitable solvents include, but are not limited to, alcohols (e.g., methanol, ethanol, n-propanol and isopropanol), alkanes (e.g., halogenated or unhalogenated alkanes such as hexane, heptane, cyclohexane, methylene chloride and chloroform), amides (e.g., dimethylformamide, N-methylpyrrolidone), ethers (e.g., tetrahydrofuran (THF), dipropyl ether and dioxolane), ketones (e.g., methyl ethyl ketone, methyl isobutyl ketone), aromatic compounds (e.g., toluene and xylene), nitriles (e.g., acetonitrile), and ester (e.g., ethyl acetate and butyl acetate). THF and chloroform have been shown to be preferred solvents due to their excellent solvency for a variety of polymers and bioactive agents.

Any of the polymer compositions described herein can be provided to the surface of the medical article and can include any number of desired bioactive agents, depending upon the final application of the medical device. The coating of polymeric material (with or without bioactive agent) can be applied to the medical device using standard techniques to cover the entire surface of the device, or a portion of the device surface. Further, the polymeric material can be provided as a single layer of polymer, or as multiple layers of polymeric material. In some cases the polymeric material can be applied as a layer with out the bioactive agent. When multiple polymeric layers are provided on the surface, each individual layer of polymer can be chosen to provide a desired effect. Thus, in some embodiments, one or more of the polymeric layers is composed of a polymeric material that is different from one or more of the other layers. Alternatively, each polymeric layer is composed of the same polymeric materials. Additionally, multiple layers of various bioactive agents can be deposited onto the medical device surface so that a particular bioactive agent can be presented to or released from the medical device at one time, one or more bioactive agents in each layer, which can be separated by polymeric material.

Application techniques for the coating of polymeric material include, for example, dipping, spraying, and the like. The suitability of the polymeric composition for use with a particular medical article, and in turn, the suitability of the application technique, can be evaluated by those skilled in the art, given the present description.

The invention provides methods for preparing a biocompatible surface on a medical article. According to the invention, biocompatible agents can be selected to improve the compatibility (for example, with blood and surrounding tissues) of medical device surfaces. In preferred embodiments, the biocompatible agent, when coupled to the medical device surface, can serve to shield the blood from the underlying medical device material. Suitable biocompatible agents preferably reduce the likelihood for blood components to adhere to the medical device and activate, thus reducing the formation of thrombus or emboli (blood clots that release and travel downstream).

The biocompatible agent can be essentially any biomolecule that is attached to the solid surfaces of medical articles to improve biocompatibility of the medical article. Thus, the description of bioactive agents suitable for use in the polymeric material is instructive for selection of the biocompatible agents as well.

The biocompatible agent can be a biocompatible polymer, which can be essentially any polymer that can improve biocompatibility of the medical article.

Representative examples of biocompatible polymers (including peptides and proteins) having antithrombotic effects include heparin, heparin derivatives, sodium heparin, low molecular weight heparin, hirudin, polylysine, argatroban, glycoprotein IIb/IIIa platelet membrane receptor antibody, coprotein IIb/IIIa platelet membrane receptor antibody, recombinant hirudin, thrombin inhibitor (such as commercially available from Biogen), chondroitin sulfate, modified dextran, albumin, streptokinase, and tissue plasminogen activator (TPA).

Other contemplated biocompatible polymers include fibronectin, laminin, collagen, elastin, vitronectin, tenascin, fibrinogen, thrombospondin, osteopontin, von Willibrand Factor, bone sialoprotein, and active domains thereof, or a hydrophilic polymer such as hyaluronic acid, chitosan or methyl cellulose.

According to the invention, the biocompatible composition also includes a photoreactive moiety. The photoreactive moiety can be pendent from the biocompatible polymer, such as heparin. Alternatively, or additionally, the photoreactive moiety is independent of the polymeric material in the coating composition.

Thus, in one aspect, the invention provides methods of coupling a biocompatible agent to a surface of a medical article, the method comprising steps of providing a polymeric material on a surface of a medical article, the polymeric material comprising one or more bioactive agents; and providing biocompatible agent to the polymeric material under conditions sufficient to couple the biocompatible agent to the polymeric material. Coupling of the biocompatible agent with the polymeric material is accomplished by activating photoreactive groups provided by the polymeric material, the biocompatible agent, or both the polymeric material and the biocompatible material.

In some embodiments, a crosslinking agent can be utilized to couple a biocompatible agent to the surface. Exemplary crosslinking agents are described in Applicant's U.S. Pat. No. 5,414,075 (Swan et al.), and U.S. Publication No. 2003/0165613 A1 (Chappa et al.). See also U.S. Pat. No. 5,714,360 (Swan et al.) and U.S. Pat. No. 5,637,460 (Swan et al.).

In one such embodiment described in these references, the crosslinking agent can comprise a chemical nonpolymeric core molecule having attached to it one or more first latent reactive groups and one or more second latent reactive groups, each of the first and second latent reactive groups being attached to the backbone in such a manner that, upon activation of the latent reactive groups in the presence of a support surface, (a) the first latent reactive groups are capable of covalently bonding to the support surface, and (b) upon bonding of the first latent reactive groups to the surface, the second latent reactive groups are:

(1) restricted from reacting with either a spacer or the support surface, (2) capable of reverting to their inactive state, and (3) upon reverting to their inactive state, are thereafter capable of being reactivated.

As described in these references, the first and second latent reactive groups can be of the same or different types, and the distinction between the two can be determined under the conditions, and at the time of use. Generally, the first latent reactive groups are defined (from amongst those originally present) as those that become attached to the surface itself, which in turn, serves to define the second latent reactive groups as those that remain unattached, and hence revert to activatable form. Although these reagents are primarily described for use as grafting reagents in the referenced patent and patent publication, it has been found that these reagents can serve as crosslinking agents according to the present invention. Thus, the first latent reactive groups become attached to the surface of the medical device, while the second latent reactive groups can be utilized to couple the biocompatible agent as taught herein.

In some preferred embodiments, the crosslinking reagent is selected from tetrakis (4-benzoylbenzyl ether), the tetrakis (4-benzoylbeonzoate ester) of pentaerythritol, and an acylated derivative of tetraphenylmethane.

Alternatively, the crosslinking agent can comprise a non-polymeric core molecule having attached thereto, either directly or indirectly, one or more substituents comprising negatively charged groups, and two or more latent reactive species, wherein the latent reactive species are provided as discrete latent reactive groups. In such embodiments, the latent reactive species can comprise one or more first latent reactive species adapted to couple to the surface of the medical device, and one or more second latent reactive (photoreactive) species adapted to couple the biocompatible agent. Suitable reagents of this type are described, for example, in Applicant's International Patent Application No. US 99/21247.

In one such embodiment, the crosslinking agent comprises a conjugated cyclic diketone having attached thereto, either directly or indirectly, one or more substituents comprising negatively charged groups, and wherein each ketone group of the diketone is adapted to serve as a photoreactive moiety capable of being activated in order to provide a free radical. Preferably, the conjugated cyclic diketone is a quinone selected from substituted and unsubstituted benzoquinone, camphroquinone, naphthoquinone, and anthraquinone.

Such reagents typically comprise a non-polymeric core molecule having attached thereto, either directly or indirectly, one or more substituents comprising negatively charged groups, and two or more latent reactive species, wherein the latent reactive species are provided as discrete photoreactive groups. In preferred embodiments, the crosslinking agents of this embodiment are selected from the group 4,5-bis(4-benzoylphenylmethyleneoxy) benzene-1,3-disulfonic acid dipotassium salt (DBDS); 2,5-bis(4-benzoylphenylmethyleneoxy) benzene-1,4-disulfonic acid dipotassium salt (DBHQ); a hydroquinone monosulfonic acid derivate, an anthraquinone sulfonic acid salt; and a camphorquinone derivative.

In another alternative embodiment, a crosslinking reagent of the invention can be provided in the form of a reagent of the general formula:

Wherein each X is independently a radical containing a latent reactive (for example, photoreactive) group and Y is a radical containing one or more charged groups. Such reagents are described, for instance, in U.S. Pat. No. 5,714,360 (Swan et al.) and U.S. Publication No. US 2003/0165613 (Chappa et al.) (each commonly assigned to the present assignee).

A reagent of this type includes one or more charged groups, and optionally one or more additional latent reactive groups, included in the radical identified in the formula as "Y." A "charged" group, when used in this sense, refers to groups that are present in ionic form, that is, that carry an electrical charged under the conditions (for example, pH) of use. The charged groups are present, in part, to provide the compound with the desired water solubility.

Preferred Y groups are non-polymeric, that is, they are not formed by polymerization of any combination of monomers. In some aspects, non-polymeric agents are preferred since they will tend to have lower molecular mass, which in turn means that they can generally be prepared to have a higher concentration of latent reactive groups per unit mass. In turn, they can generally provide a higher coating density of latent reactive groups than comparable latent reactive polymeric agents.

The type and number of charged groups in a preferred reagent are sufficient to provide the agent with a water solubility (at room temperature and optimal pH) of at least about 0.1 mg/mL, or at least about 0.5 mg/mL, or at least about 1 mg/mL. Given the nature of the surface coating process, crosslinking solubility levels of at least about 0.1 mg/mL are generally adequate for providing useful coatings of crosslinking agent on surfaces.

Examples of suitable charged groups include, but are not limited to, salts of organic acids (such as sulfonate, phosphonate, and carboxylate groups), onium compounds (such as quaternary ammonium, sulfonium, and phosphonium groups), and protonated amines, as well as combinations thereof. An example of an agent employing charged groups other than quaternary ammonium compounds is provided in Formula X of Table I in U.S. Pat. No. 5,714,360 (Swan et al.).

A preferred charged group for use in preparing crosslinking agents according to the invention is a quaternary ammonium group. The term "quaternary ammonium" as used herein, refers to organic derivatives of $NH_4^+$ in which the hydrogen atoms are each replaced by radicals, thereby imparting a net positive charge on the radical. The remaining counter-ion can be provided by any suitable anionic species, such as a chloride, bromide, iodide, or sulfate ion.

In a preferred embodiment, two or more photoreactive groups can be provided by the X groups attached to the Y radical. Preferred reagents of this type are described in U.S. 2003/0165613 A1.

In still further embodiments, the crosslinking agent can comprise a non-polymeric core molecule having attached thereto, either directly or indirectly, one or more substituents comprising positively charged groups, and two or more latent reactive species, wherein the latent reactive species are provided as discrete latent reactive groups. In such embodiments, the latent reactive species can comprise one or more first latent reactive species adapted to couple to the surface of the medical device, and one or more second latent reactive (photoreactive) species adapted to couple the biocompatible agent. In one preferred embodiment, the crosslinking agent comprises tetramethylethylenediamine-diMBP-quat.

Exemplary crosslinking agents are also disclosed in U.S. Pat. No. 6,669,994 (Swan et al., commonly assigned to the assignee of the present invention).

A "latent reactive group," as used herein, refers to a chemical group that responds to an applied external energy source in order to undergo active specie generation, resulting in covalent bonding to an adjacent chemical structure (via an abstractable hydrogen). Preferred groups are sufficiently stable to be stored under conditions in which they retain such properties. See, for example, U.S. Pat. No. 5,002,582 (Guire et al.). Latent reactive groups can be chosen that are responsive to various portions of the electromagnetic spectrum, with those responsive to ultraviolet and visible portions of the spectrum (referred to herein as "photoreactive") being particularly preferred.

Photoreactive species response to a specific applied external ultraviolet or visible light source to undergo active specie generation with resultant covalent bonding to an adjacent chemical structure, for example, as provided by the same or a different molecule. Photoreactive species are those groups of atoms in a molecule that retain their covalent bonds unchanged under conditions of storage but that, upon activation by a specific applied external ultraviolet or visible light source form covalent bonds with other molecules.

Latent reactive (for example, photoreactive) species generate active species such as free radicals and particularly nitrenes, carbenes, and excited states of ketones, upon absorption of electromagnetic energy. Latent reactive species can be chosen to be responsive to various portions of the electromagnetic spectrum, and photoreactive species that are responsive to the ultraviolet and visible portions of the spectrum are preferred and can be referred to herein as "photochemical groups" or "photogroups."

The latent reactive species in latent reactive aryl ketones are preferred, such as acetophenone, benzophenone, anthraquinone, anthrone, and anthrone-like heterocycles (for example, heterocyclic analogs of anthrone such as those having nitrogen, oxygen, or sulfur in the 10-position), or their substituted (for example, ring substituted) derivatives. Examples of preferred aryl ketones include heterocyclic derivatives of anthrone, including acridone, xanthone, and thioxanthone, and their ring substituted derivatives. Particularly preferred are thioxanthone, and its derivatives, having excitation energies greater than about 360 nm.

The functional groups of such ketones are preferred since they are readily capable of undergoing the activation/inactivation/reactivation cycle described herein. Benzophenone is a particularly preferred latent reactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (for example, carbon-hydrogen) is not available for bonding, the ultraviolet light-induced excitation of the benzophenone group is reversible and the molecule returns to ground state energy level upon removal of the energy source. Photoactivatable aryl ketones such as benzophenone and acetophenone are of particular importance inasmuch as these groups are subject to multiple reactivation in water and hence provide increased coating efficiency.

Crosslinking agents as described herein can be used to modify any suitable surface. Where the latent reactive group of the crosslinking agent is a latent reactive (for example, photoreactive) group of the preferred type, the support surface to be coated preferably provides abstractable hydrogen atoms suitable to enable covalent bonding with the activated group. In another embodiment, the surface can be modified (for example, by pretreatment with a suitable reagent) to provide abstractable hydrogen atoms on the surface.

The crosslinking agent can physically adhere to a target, such as a coated layer or surface, by hydrophobic interactions. Upon illumination, the photoreactive groups (for example, benzophenone groups) undergo covalent bond formation at the layer or surface. With the absence of abstractable hydrogen atoms in proximity to the remaining unbonded photoreactive group(s), and removal of the illumination source, the excited state benzophenone returns to ground state energy. These remaining groups can then be reactivated when the biocompatible agent to be coupled is present and when the treated surface is exposed to another round of illumination. This method can be described as a "two-step" approach, where the photoreactive crosslinking agent is applied in the first step to create a latent reactive surface on the medical device, and in the second step, the biocompatible agent is coupled to the activated surface.

The preparation of polymers having photoreactive groups can be carried out by any one of a variety of methods that are known in the art. A polymer having photo-reactive groups can be synthesized by first preparing a polymeric portion, which can subsequently be coupled to a photoreactive group. For example, in one embodiment, the polymeric portion of the photopolymer is formed by reacting acrylamide, 2-acrylamide-2-methylpropane sulfonic acid, and N-(3-aminopropyl) methacrylamide. In another embodiment, the polymeric portion is prepared by the copolymerization of 1-vinyl-2-pyrrolidone and N-(3-aminopropyl) methacrylamide. The copolymers are derivatized with an acyl chloride (such as, for example, 4-benzoylbenzoyl chloride) under Schotten-Baumann conditions to form photo-poly(vinylpyrrolidone) (also referred to as "photo-PVP"). That is, the acyl chloride reacts with the amino group of the N-(3-aminopropyl) moiety of the copolymer. An amide is formed resulting in the attachment of the aryl ketone to the polymer. The liberated hydrochloric acid is neutralized with an aqueous base solution.

Photoderivatized polysaccharides, such as heparin ("photo-heparin") can be prepared by those skilled in the art as well, for example, in the manner described in U.S. Pat. No. 5,563,056 (Swan et al., see Example 4), which describes the preparation of photo-heparin by reacting heparin with benzoyl-benzoyl-epsilon-aminocaproyl-N-oxysuccinimide in dimethylsulfoxide/carbonate buffer. The solvent was evaporated and the photo-heparin was dialyzed against water, lyophilized, and then dissolved in water.

In other aspects, the invention provides methods of preparing a biocompatible surface that includes a polymeric material containing a bioactive agent, the method comprising steps of determining information indicative of wavelength of light that causes inactivation of the bioactive agent, and using the wavelength information obtained to select a filter for coupling photoreactive agents to the polymeric material containing the bioactive agent. According to these embodiments, inactivation of the bioactive agent means degradation of the bioactive agent sufficient to reduce or eliminate the therapeutic effectiveness of the bioactive agent.

In one such embodiment, for example, a medical article having a polymeric material disposed on at least a portion of its surface is provided, wherein the polymeric material includes a bioactive agent. In these embodiments, wavelength that the bioactive agent maximally absorbs light is determined to assess the potential for light irradiation to degrade the bioactive agent. For example, it can be determined that the bioactive agent is subject degradation when irradiated with wavelengths in the range of 300 nm or less. Exemplary compounds that may be subject to degradation when irradiated with wavelengths of less than 300 nm include, but are not limited to, sirolimus (rapamycin; $A_{max}$=~290 nm), analogs of rapamycin ("rapalogs"), tacrolimus, ABT-578, everolimus, paclitaxel ($A_{max}$=~231 nm), and taxane.

This information can be utilized in combination with information relating to electromagnetic energy sufficient to activate photoreactive agents (for example, to undergo active specie generation with resultant covalent bonding to an adjacent chemical structure) as described herein (for example, having activation wavelengths in the UV and visible portions of the spectrum, such as in the range of 100-700 nm, or 300-600 nm, or 200-400 nm, or 300-340 nm). An amount of energy can be applied to the surface of the medical article in conjunction with a desired filter to promote formation of the coating via the photo-reactive groups, yet cause minimal degradation of the bioactive agent in the coating.

Figure 5:
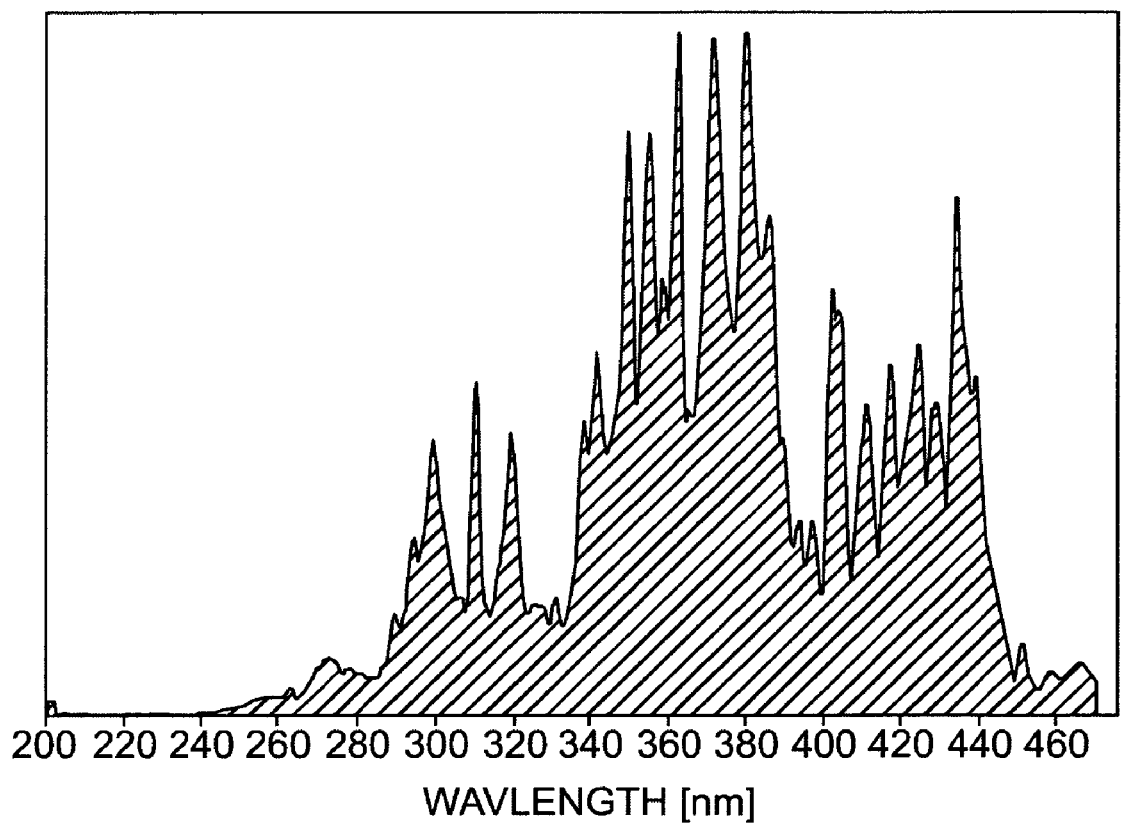
FIG. 5 is an output spectrum for a metal halide "D" (iron) bulb for a UV curing system.

A light source is used that provides output radiation sufficient to activate the photoreactive groups and promote formation of the coating. Suitable light sources can incorporate, for example, metal halide bulbs, or other suitable bulbs that provide an activating source of irradiation. One suitable light source is a Dymax Blue Wave Spot Cure System, which has an output spectrum as shown in FIG. 5.

In some aspects an amount of energy in the range of about 0.12 J/cm$^2$ to about 0.96 J/cm$^2$ as measured at 335 nm, is applied to the surface; a more preferable range is from about 0.12 J/cm$^2$ to about 0.72 J/cm$^2$. Other ranges can be used in conjunction with the step of forming the coating. In various embodiments, these ranges can have a lower end of about 0.12 J/cm$^2$, about 0.18 J/cm$^2$, or about 0.36 J/cm$^2$, to an upper end of about 0.45 J/cm$^2$, about 0.54 J/cm$^2$, about 0.72 J/cm$^2$, or about 0.96 J/cm$^2$. The combined information can then be utilized to select an appropriate light filter for application of photoreactive species to the polymeric material.

Information relating to the UV spectra at which a particular bioactive agent is degraded can be obtained, for example, by the provider of the bioactive agent, or by subjecting the bioactive agent to a variety of wavelengths of light, and determining the subsequent activity retained of the bioactive agent.

Typically, filters are identified by the wavelength of light that is permitted to pass through the filter. Exemplary types of filters that can be used in connection with the invention include those selected from ultra-violet cut-off filters, ultra-violet transmitting filters, band pass filters, and colored filters. Generally, ultra-violet cut-off filters are categorized by a ultra-violet cut-off transmittance, at which the light transmittance is approximately 25% of the maximum transmittance. FIG. 1 shows the percent transmittances over a range of wavelengths of various ultra-violet cut-off filters. A preferred ultra-violet cut-off filter has a cut-off transmittance (25% of maximum transmittance at about 320 nm and above, and preferably in the range of about 320 nm to 330 nm.

Figure 2:
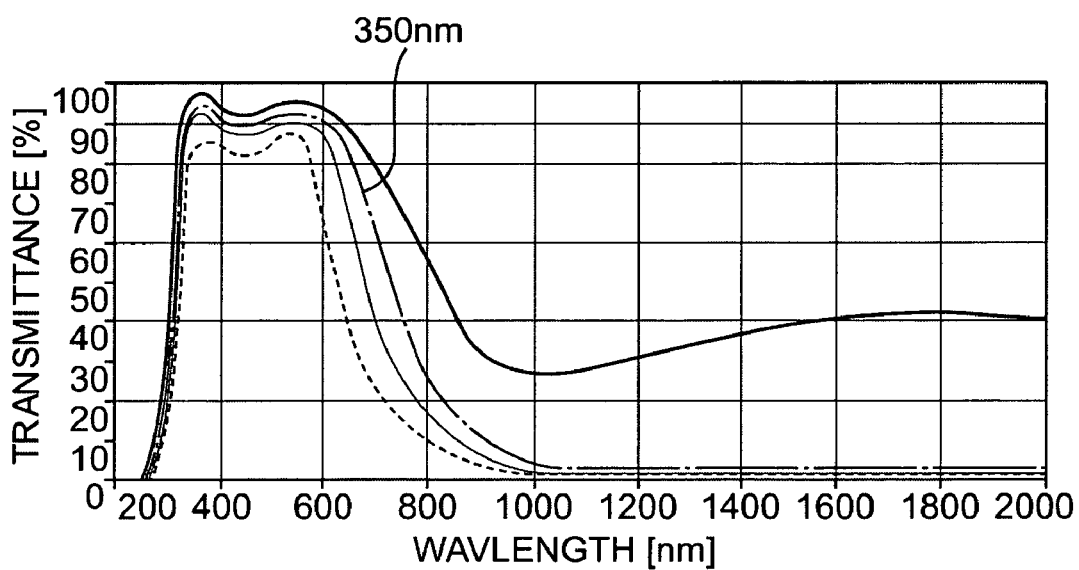
FIG. 2 is a graph of percent transmittance over a spectrum of wavelengths for various ultra-violet transmitting filters.

Generally, ultra-violet transmitting filters are categorized by a peak transmitting wavelength; the transmittance of wavelengths to the left of the peak (shorter wavelengths) generally drops off sharply. FIG. 2 shows the percent transmittances over a range of wavelengths of various ultra-violet transmitting filters. A preferred ultra-violet transmitting filter has a peak wavelength above 320 nm.

Figure 3:
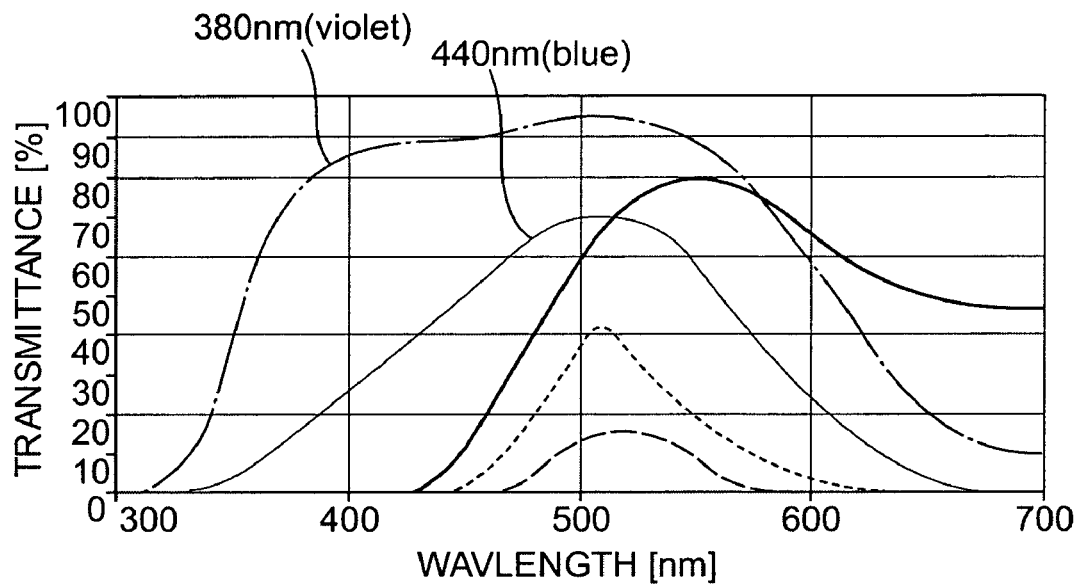
FIG. 3 is a graph of percent transmittance over a spectrum of wavelengths for various colored filters.

Generally, colored filters are also categorized by the presence of a glass portion of the filter being visibly colored. FIG. 3 shows the percent transmittances over a range of wavelengths of various colored filters. Preferred colored filters include 380 nm (violet) and 440 nm (blue) filters.

Figure 4:
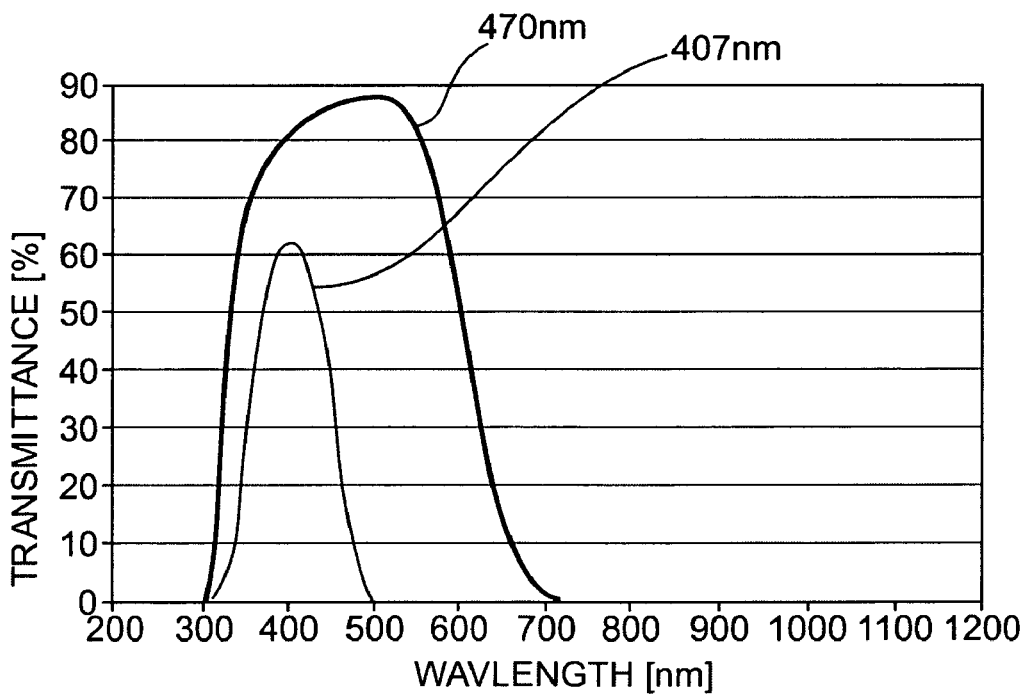
FIG. 4 is a graph of percent transmittance over a spectrum of wavelengths for various bandpass filters.

For band pass filters, a range of wavelength is identified for the filter, and the center wavelength is the midpoint of wavelength allowed through; at midpoint, the transmittance is approximately half of the maximum transmittance allowed through the filter. FIG. 4 shows the percent transmittances over a range of wavelengths of various band pass filters. Preferred band pass filters filter have a center wavelength above about 380 nm, and preferably in the range of about 380 to about 470 nm.

Thus, in one embodiment utilizing a band pass filter, for example, an Edmund 407 nm filter, the filter can be chosen that has a maximum UV transmittance at its center wavelength of 407 nm. From either direction from that, the UV transmittance decreases. Thus, towards 300 nm, the UV transmittance is not enough to cause significant degradation of the rapalog. This filter can be selected and utilized to couple a photoreactive reagent to a polymeric material containing rapamycin or a rapalog, as shown in the Examples. Other exemplary embodiments of this aspect of the invention can be found in the examples.

The invention will be further described with reference to the following non-limiting Examples.

EXAMPLES

For the following examples, the following standard reagents and nomenclature are adopted:

Compound I (Tetrakis(4-benzoylbenzyl ether) of pentaerythritol (TBBE)

25
Compound II (4,5-bis-4-benzoyl-phenylmethyl-eneoxy)benzene-1,3-disulfonic acid dipotassium salt (DBDS)
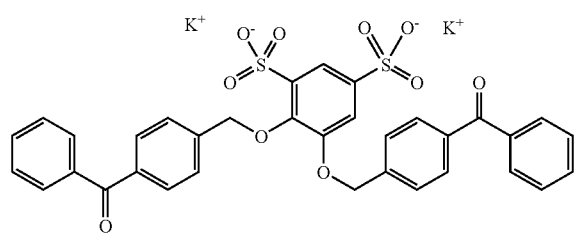
26
Compound V (photo-polyvinylpyrrolidone copolymer) (Photo-PVP)
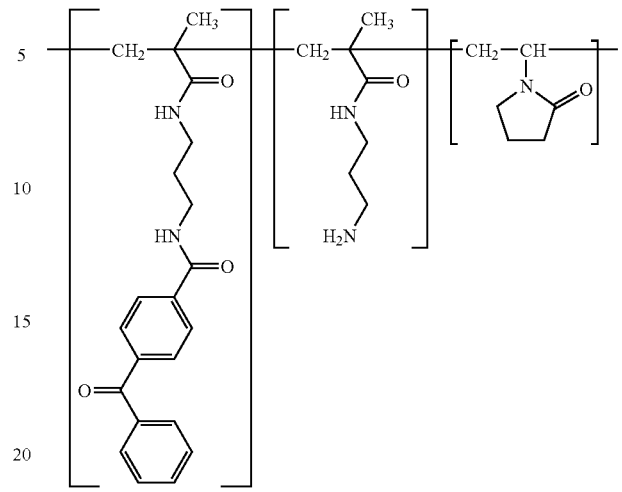
Compound III (Tetramethylethylenediamine-diMBP-quat. (TEMED-DQ)
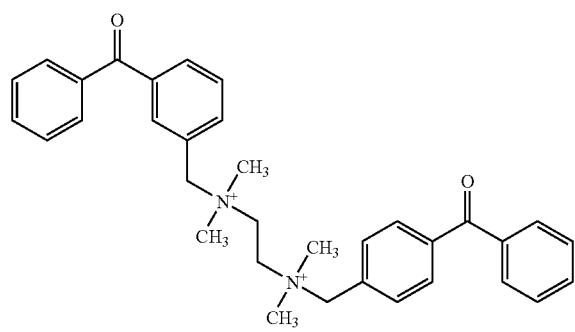
Compound VI (Acetylated PVP-AMPA-BBA) (Acetylated Photo-PVP)
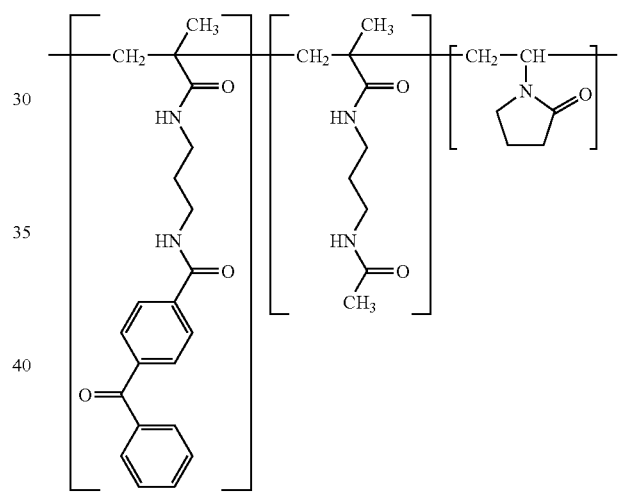
Compound IV (BBA-EAC-Heparin)
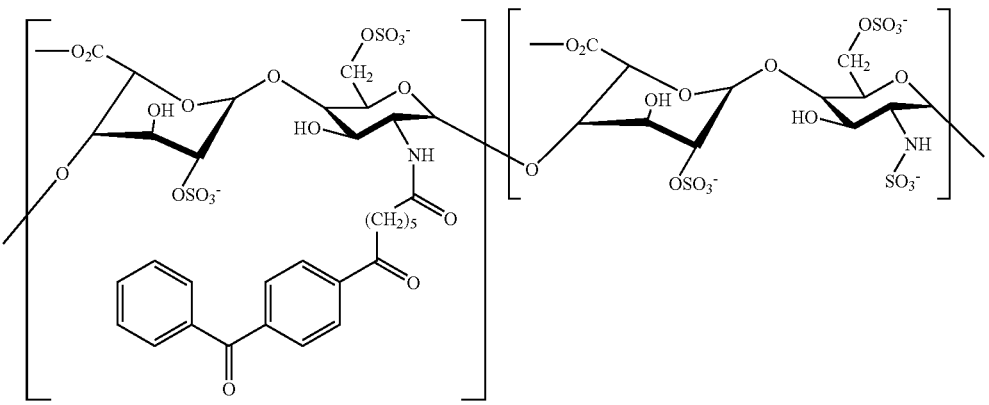

For all examples, stents had a surface area of 0.8757 cm². Medical device surface areas, including stent surface areas, can be calculated based on the diameter, the length, and the overall configuration of the medical device. Surface areas can also be obtained from the manufacturer of the medical device.

Stents described as having a coating of Parylene™, polylactic acid (PLA), or ethylene vinyl alcohol (EVAL) comprised stents having the identified coatings physically adhered to their surface, utilizing known stent coating techniques.

For all examples, UV intensity was measured using a radiometer (International Light) filtered to measure intensity at 330-340 nm.

In the Examples, the following standard techniques were used:

Immersion Coating Procedure

Coating solutions were prepared by dissolving photo-heparin (Compound IV) or acetylated photo-PVP (Compound VI) at desired concentrations as described herein in deionized water. Stents were immersed in the reagent solution, allowed to dwell 5 to 10 seconds in solution, then illuminated for 60 seconds utilizing a Dymax Blue Wave Spot Cure System (light system commercially available from Dymax). The ultraviolet wand was placed at a distance to provide the stents with approximately 0.5-25 mW/cm² in the wavelength range 330-340 nm. The stents were gently agitated by hand during the 60 seconds of illumination to ensure that the surface was evenly bathed in light. The stents were then removed from the coating solution. After removal of the stents from the coating solution, the stents was rinsed with deionized water, blown with nitrogen gas to remove large drops of solution, then air dried (for at least 2 minutes, up to overnight air drying) until the solvent was no longer visible.

Spray Coating Procedure

The following spray coating procedure was followed in order to deposit a heparin-containing composition on the stents. The coating procedure was performed in order to provide stents with a desired amount of solids from the photo-heparin composition.

The parts were placed on a roller system such as that described in U.S. patent application Ser. No. 10/256,349 ("Advanced Coating Apparatus and Method," Chappa et al., filed Sep. 27, 2002). The device rotator included a pair of rollers suitable for holding the stent, the pair having first and second rollers arranged substantially parallel to each other and separated by a gap. The spray nozzle was operationally arranged to produce spray of a coating material directed at the gap and, when the device is not positioned on the pair of rollers, arranged so the majority of the spray was passed through the gap. In use, a heparin-containing composition was disposed on the device from the spray nozzle, and the majority of any spray that did not get deposited on the device was passed through the gap. The stent was then rotated by rotation of the rollers to position a different portion of the device for subsequent application of the heparin-containing composition. Coating was applied to the stent at a rate in the range of 0.03 ml/min to 0.2 ml/min. The spray nozzle utilized was an ultrasonic nozzle, such as that commercially available from Sonotek (Ultrasonic spray coater) and described in U.S. patent application Ser. No. 10/256,349. The coating parameters were as follows. The spray nozzle moved over stents at a rate of 50-150 mm/sec. The spray head passed over the stent 10-120 times (described as the number of "passes"; 2 passes equals 1 cycle), as indicated. The total number of passes was selected to provide a final coated weight of 70-150 mg/stent. Also, the stent was rotated during the spray coating process a sufficient number of times to provide a uniform coating on the surface (typically, the stent was rotated a minimum of 2 revolutions per coating application). The spray coatings were applied in a low humidity environment (less than 20% humidity). The coating solution was supplied from the spray nozzle at a pressure in the range of 1-3 psi.

Quantity of Coated Heparin

Generally, using the coating techniques as described, heparin in an amount of about 100 μg was applied to the stents in the coating.

Heparin Activity Assay

The antithrombotic activity of heparin is due to its inhibition of thrombin, which is a protease that is known to participate in the clotting cascade. Heparin inhibits thrombin activity by first binding to antithrombin III (ATIII). The heparin/ATIII complex then binds to and inactivates thrombin, after which the heparin is released and can bind to another ATIII. The assay for inhibition of thrombin by immobilized heparin was conducted by measuring the cleavage of a chromogenic peptide substrate by thrombin.

Prior to performing the Heparin Activity Assay, coated stents were washed overnight (12-18 hours) to remove any unbound material from the coated stents. Coated stents were washed in diH₂O or PBS at a temperature of about 37° C. on an orbital shaker (set for gentle agitation).

Each assay was conducted in 1 mL of PBS that contained 0.85 mg BSA (Sigma Chemical Co.), 10 mU human thrombin (Sigma Chemical Co.), 100 mU/mL ATIII (Baxter Biotech, Chicago, Ill.), and 0.17 μmole of the chromogenic thrombin substrate S-2238 (Kabi Pharmacia, Franklin, Ohio). To this assay solution was added either uncoated or heparin coated stents (to evaluate heparin activity on the membranes) or standard concentrations of heparin (to generate standard curves of heparin content versus absorbance). For standard curves, the amounts of heparin that were added ranged from 2.5 mU to 25 mU. The color generated, measured as absorbance at 405 nm, by thrombin mediated cleavage of the S-2238 was read using a spectrophotometer after 2 hours of incubation at 37° C. The absorbance was directly related to the activity of the thrombin and, thus, inversely related to the amount of activation of ATIII induced by the heparin in solution or immobilized on the surface of the substrate. Activity of surface bound heparin was calculated by comparing the absorbance values generated with the membranes to the absorbance values generated with known amounts of added heparin.

Commercial preparations of heparin are commonly calibrated in USP units, 1 unit being defined as the quantity that prevents 1.0 mL of citrated sheep plasma from clotting for 1 h after the addition of 0.2 mL of 10 g/L $CaCl_2$ (see Majerus PW, et al. Anticoagulant, thrombolytic, and antiplatelet drugs. In: Hardman JG, Limbrid LE, eds., Goodman and Gilman's The pharmacological bases of therapeutics, 9th ed, New York: McGraw Hill, 1996:1341-6). Commercial preparations of heparin typically include the heparin activity of the preparation. In order to determine the heparin activity of a heparin coating described herein, the above assay can be performed and compared to a standard generated from a commercial preparation of heparin, based on the above definition of heparin activity.

Controls

Metal stents containing a coating of Parylene™ were immersed in a solution of photo-heparin and coated using the Immersion Coating and Spray Coating Procedures described above. The base coat solution applied was 25 mg/mL photo-heparin in water. Spraycoat solution applied was 50 mg/mL in water. Mean heparin activity was 31 mU/cm².

Stents containing a coating of ethylene vinyl alcohol and drug were coated with photo-heparin using the Immersion Coating and Spray Coating Procedures described above. During the post-spraying illumination, the stents were illuminated through an Oriel 324 nm filter. The first coat (applied by Immersion Coating Procedure) was 25 mg/mL photo-heparin in water, and the outer coating (applied by Spray Coating Procedure) was 50 mg/mL photo-heparin in water. Mean heparin activity was 32 mU/cm².

For Samples 1-F(1) and 1-F(2) the dwell time in solution during the immersion was extended to 5 minutes although irradiation during this immersion is as indicated in the table.

TABLE 1

| Sample No. | Illumination In-solution/post-spray (seconds) | Filter (Post-spray illumination) | UV intensity @ 335 nm | UV dose | Heparin activity (mU/cm²) |
|---|---|---|---|---|---|
| 1-A(1) | 45/45 | Oriel 324 nm Cut-off | 6-8 mW/cm² | 0.54-0.72 J/cm² | 26 |
| 1-A(2) | 45/45 | Oriel 324 nm Cut-off | 6-8 mW/cm² | 0.54-0.72 J/cm² | 22 |
| 1-B | 30/30 | Oriel 324 nm Cut-off | 6-8 mW/cm² | 0.36-0.48 J/cm² | 20 |
| 1-C | 60/60 | Edmund 407 nm Bandpass | 1-1.3 mW/cm² | 0.12-0.156 J/cm² | 24 |
| 1-D | 45/45 | Edmund 470 nm Bandpass | 4-5 mW/cm² | 0.36-0.45 J/cm² | 17 |
| 1-E | 60/60 | Opto Sigma 380 Short wave cut off | 0.02-0.04 mW/cm² | 24-48 mJ/cm² | 2 |
| 1-F(1) | 60/60 | Oriel 324 nm Cut-off | 6-8 mW/cm² | 0.72-0.96 J/cm² | 24 |
| 1-F(2) | 60/60 | Oriel 324 nm Cut-off | 6-8 mW/cm² | 0.72-0.96 J/cm² | 25 |
| 1-G(1) | 45/45 | Opto Sigma 380 nm Colored glass | 4-5 mW/cm² | 0.36-0.45 J/cm² | 31 |
| 1-G(2) | 45/45 | Opto Sigma 380 nm Colored glass | 4-5 mW/cm² | 0.36-0.45 J/cm² | 29 |
| 1-H(1) | 45/45 | Opto Sigma 370 nm Colored glass | 2-3 mW/cm² | 0.18-0.27 J/cm² | 26 |
| 1-H(2) | 45/45 | Opto Sigma 370 nm Colored glass | 2-3 mW/cm² | 0.18-0.27 J/cm² | 30 |
| 1-I(1) | 60/60 | Opto Sigma 400 nm Colored glass | 1-1.5 mW/cm² | 0.12-0.18 J/cm² | 33 |
| 1-I(2) | 60/60 | Opto Sigma 400 nm Colored glass | 1-1.5 mW/cm² | 0.12-0.18 J/cm² | 30 |
| 1-J(1) | 30/30 | Opto Sigma 440 nm Colored glass | 6-8 mW/cm² | 0.36-0.48 J/cm² | 30 |
| 1-J(2) | 30/30 | Opto Sigma 440 nm Colored glass | 6-8 mW/cm² | 0.36-0.48 J/cm² | 33 |
| 1-K(1) | 60/60 | Opto Sigma 500 nm Colored glass | 6-8 mW/cm² | 0.72-0.96 J/cm² | 26 |
| 1-K(2) | 60/60 | Opto Sigma 500 nm Colored glass | 6-8 mW/cm² | 0.72-0.96 J/cm² | 24 |

Example 1

Stents having a coated layer of ethylene vinyl alcohol (E/VAL) that contained a rapamycin analog, in the examples referred to as a "rapalog", were used as substrates for photo-heparin coating. Methods for preparing stents having an ethylene vinyl alcohol (E/VAL) coating are described in U.S. Pat. No. 6,759,054. Immersion coating and spray coating with modifications as follows were used to form photo-heparin layers on these (E/VAL)/rapalog coated stents.

For all samples, a first photo-heparin coated layer was formed on the (E/VAL)/rapalog layer by immersion coating by immersing the stents in 25 mg/mL photo-heparin in water. Irradiation was carried out while the stents were immersed in solution. The irradiation time during immersion is indicated in Table 1.

A second photo-heparin layer was formed by applying photo-heparin by spray coating at a concentration of 50 mg/mL in water. The stents were then illuminated for a period of time and with a UV filter as indicated in Table 1. UV intensity was measured at 335 nm. The total UV intensity applied to the stents Results illustrated that utilization of a filter when illuminating the coating materials allowed the improved coupling with photo-heparin, and thus higher heparin activity. A wide array of filters were utilized that may be important when used in combination with a device having a base polymeric material layer (such as E/VAL) that includes one or more drugs that are sensitive to illumination with light in certain wavelength ranges.

For samples 1-F(1) and 1-F(2), the longer dwell time and illumination time in solution and higher intensity of light applied to couple the heparin to the EVAL resulted in a higher loss/degradation of the rapalog contained in the polymeric material (about 50% loss/degradation).

Generally, the amount of drug degradation increased when the amount of radiation was near 0.96 J/cm².

For sample 1-B, a shorter illumination time, coupled with a shorter dwell time, and a 324 nm filter resulted in lower degradation of the rapalog contained in the polymeric material (less than 5% degradation)

For sample 1-C, utilization of an Edmund 407 nm filter, and a lower UV intensity resulted in lower degradation of the rapalog contained in the polymeric material (less than 5% degradation). .

Example 2

Stents having a coated layer of polylactic acid (pLA) that contained a rapamycin analog as (the rapamycin analog as described in Example 1) were used as substrates for photo-heparin coating. Immersion coating and spray coating with modifications as follows were used to form photo-heparin layers on these pLA/rapalog coated stents.

For all samples, a first photo-heparin coated layer was formed on the pLA/rapalog layer by immersion coating by immersing the stents in 25 mg/mL photo-heparin in water. Irradiation was carried out while the stents were immersed in solution. The irradiation time during immersion is indicated in Table 2.

A second photo-heparin layer was formed by applying photo-heparin by spray coating at a concentration of 50 mg/mL in water. The stents were then illuminated for a period of time and with a UV filter as indicated in Table 2.

by immersing the stents in 5 mg/mL photo-PVP in water. Irradiation was carried out while the stents were immersed in solution. The irradiation time during immersion is indicated in Table 2. After illumination in solution, the stents were removed, air dried.

For samples 3-A(1) and 3-A(1), photo-heparin was applied as described above by spray coating using a concentration of photo-heparin of 50 mg/mL in water. For sample 3-B, heparin was sprayed onto the parts in a concentration of 4 mg/mL photo-heparin in THF/H$_2$O (92/8). Stents were then illuminated under the following conditions post-spray.

TABLE 2

| Sample No. | Illumination In-solution/post-spray (seconds) | Filter (Post-spray illumination) | UV intensity | UV dose | Heparin activity (mU/cm$^2$) |
|---|---|---|---|---|---|
| 2-A(1) | 30/30 | Oriel 324 nm | 6-8 mW/cm$^2$ | 0.36-0.48 J/cm$^2$ | 2 |
| 2-A(2) | 30/30 | Oriel 324 nm | 6-8 mW/cm$^2$ | 0.36-0.48 J/cm$^2$ | 3 |
| 2-B(1) | 45/45 | Oriel 324 nm | 6-8 mW/cm$^2$ | 0.54-0.72 J/cm$^2$ | 1 |
| 2-B(2) | 45/45 | Oriel 324 nm | 6-8 mW/cm$^2$ | 0.54-0.72 J/cm$^2$ | 2 |

These results demonstrate that utilizing the coating conditions noted in this Example, the pLA/rapalog layer did not couple heparin as readily, and thus these had a lower heparin activity (comparison is made to the heparin activities of Example 1 using stents having an (E/VAL)/rapalog layer.

TABLE 3

| Sample No. | Illumination In-solution/post-spray (seconds) | Filter (Post-spray illumination) | UV intensity | UV dose | Heparin activity (mU/cm$^2$) |
|---|---|---|---|---|---|
| 3-A(1) | 45/45 | Oriel 324 nm | 6-8 mW/cm$^2$ | 0.54-0.72 J/cm$^2$ | 37 |
| 3-A(2) | 45/45 | Oriel 324 nm | 6-8 mW/cm$^2$ | 0.54-0.72 J/cm$^2$ | 37 |
| 3-B | 60/60 | Edmund 407 nm | 6-8 mW/cm$^2$ | 0.72-0.96 J/cm$^2$ | 32 |

Results show significantly improved heparin binding by using a primer coating of a photoreactive polymer prior to applying heparin to the device. Thus, a higher heparin activity is seen for the devices including a priming layer of photoreactive polymer (photoreactive polyvinylpyrrolidone).

Example 3

Stents having a coated layer of polylactic acid (pLA) that contained a rapamycin analog as described in Example 2 were used as substrates for photo-heparin coating. Immersion coating and spray coating with modifications as follows were used to form a photo-PVP layer and then a photo-heparin layer, respectively, on these pLA/rapalog coated stents.

For all samples, a first acetylated photo-PVP coated layer was formed on the pLA/rapalog layer by immersion coating

Example 4

Stents having a coated layer of polylactic acid (pLA) that contained a rapamycin analog as described in Example 2 were used as substrates for photo-heparin coating. Photoreactive heparin was provided in various solutions of THF/water and either spray coated or immersion coated onto the pLA/rapalog stents.

The photo-heparin coating solutions were spray coated onto the stents, with the exception of Sample D-4, in which the stent was immersed in a solution of photo-heparin (25 mg/mL in H$_2$O), then sprayed with photo-heparin (concentration shown in the Table below), followed by post-spray illumination under the conditions shown below. All stents utilized an Edmund 407 run filter for post-spray illumination, and UV intensity for all samples was 1-1.3 mW/cm$^2$.

TABLE 4

| Sample No. | Spray applications | Post-spray illumination (seconds) | THF/H$_2$O (v/v) | Photo-heparin (mg/mL) | Heparin activity (mU/cm$^2$) |
|---|---|---|---|---|---|
| 4-A | 1 | 60 | 80/20 | 5.5 | 4 |
| 4-B | 1 | 60 | 80/20 | 5.5 | 4 |
| 4-C | 1 | None | 80/20 | 5.5 | 4 |
| 4-D | 1 | 60 | 80/20 | 5.5 | 7 |
| 4-E | 2 | 60 | 80/20 | 5.5 | 0 |
| 4-F | 3 | 60 | 80/20 | 5.5 | 1 |
| 4-G | 1 | 60 | 80/20 | 5.5 | 0 |
| 4-H | 2 | 60 | 80/20 | 5.5 | 0 |
| 4-I | 1 | 60 | 92/8 | 4 | 6 |
| 4-J | 2 | 60 | 92/8 | 4 | 9 |
| 4-K | 1 | 60 | 83/17 | 8 | 0 |
| 4-L | 2 | 60 | 83/17 | 8 | 0 |

Results indicated that use of the THF/H$_2$O solvent system did not improve the retention of heparin activity of the coating compositions. However, increased concentration of THF in the solvent improved heparin coating on the PLA coated stents (see samples nos. 4-I and 4-J).

Example 5

Stents having a (E/AL)/rapalog layer as described in Example 1 were used as substrates for photo-heparin coating. Various concentrations of photo-reactive heparin was provided in various solutions of THF/water and spray coated onto the (E/VAL)/rapalog stents.

Coating conditions are detailed in Table 5. All stents utilized an Edmund 407 nm filter for post-spray illumination, and UV intensity for all samples was 1-1.3 mW/cm$^2$.

TABLE 5

| Sample No. | Spray applications | Post-spray illumination (seconds) | THF/H$_2$O (v/v) | Photo-heparin conc. (mg/mL) | Heparin activity (mU/cm$^2$) |
|---|---|---|---|---|---|
| 5-A(1) | 1 | 60 | 80/20 | 5.5 | 35 |
| 5-A(2) | 1 | 60 | 80/20 | 5.5 | 38 |
| 5-B | 1 | 60 | 92/8 | 4 | 27 |
| 5-C | 1 | 60 | 92/8 | 4 | 37 |

Results indicated that utilization of photoreactive heparin in solvent containing THF with the (E/VAL) coating significantly improved retention of heparin activity. Further, improved heparin binding was seen in single coating applications (one spray coat applications for these samples).

Example 6

Stents having a coated layer of pLA/rapalog as described in Example 2 were used as substrates for coating compositions that included mixtures of photo-heparin and pLA.

Coating compositions containing PLA and photo-heparin in THF/H$_2$O (various concentrations, as indicated in Table below) were prepared and the compositions were coated onto the stents by spray coating. The PLA utilized in the coating compositions was a 50% by weight PLA/PGA copolymer. After application of the PLA/photo-heparin coating composition, all the stents were illuminated for 60 seconds through an Edmund 407 nm filter, with UV intensity for all samples in the range 1-1.3 mW/cm$^2$. For some samples, an outer coat of photo-heparin in THF/H$_2$O (various concentrations, as indicated in Table 6) was sprayed onto the stent after the PLA/photo-heparin coated stents were allowed to air dry. The outer coat of photo-heparin was applied using the spray coating and following application, stents were illuminated utilizing the same intensity light and Edmund filters as indicated for the PLA/photo-heparin coatings.

TABLE 6

| Sample No. | PLA/photo-heparin concentration THF/H$_2$O (v/v) | Photo-heparin outer coat | Heparin activity (mU/cm$^2$) |
|---|---|---|---|
| 6-A | 25 mg/mL/5 mg/mL 86/14 | None | 2 |
| 6-B | 25 mg/mL/5 mg/mL 86/14 | None | 11 |
| 6-C | 25 mg/mL/5 mg/mL 86/14 | Photo-heparin in THF/H$_2$O (92/8) | 5 |
| 6-D | 12.5 mg/mL/7.55 mg/mL 80/20 | None | 5 |
| 6-E | 12.5 mg/mL/7.55 mg/mL 80/20 | Photo-heparin in THF/H$_2$O (92/8) | 3 |
| 6-F | 6.25 mg/mL/6.25 mg/mL 80/20 | None | 3 |
| 6-G | 6.25 mg/mL/6.25 mg/mL 80/20 | Photo-heparin in THF/H$_2$O (92/8) | 3 |

Results showed that premixing polylactic acid with the heparin did not improve heparin bonding to the devices that contained a coating of PLA on their surfaces.

Example 7

In attempts to improve heparin binding and provide a biodegradable surface with heparin activity, the process of Example 6 was repeated with the exception that photo-heparin was deposited on the PLA/rapalog layer before the PLA/photo-heparin composition was disposed.

For the following samples, the stents having a PLA/rapalog layer were first coated with photo-heparin using immersion coating (1) and illuminated for 60 seconds while immersed. After the photo-heparin coat, the stents were spray coated with a PLA/photo-heparin composition (2; various concentrations, as indicated in Table 7) in THF/H$_2$O (various concentrations, as indicated in Table 7), followed by post-spray illumination for 60 seconds. The final coating was a spray coating with photo-heparin (3). All illuminations were performed through an Edmund 407 nm filter, with WV intensity in the range of 1-1.3 mW/cm². Times of illumination was 2×60 seconds (total=120 s).

TABLE 7

| Sample No. | (1) Photo-heparin immersion coating | (2) PLA/photo-heparin spray coating | (3) Photo-heparin spray coating (outer coat) | Heparin activity (mU/cm²) |
|---|---|---|---|---|
| 7-A | One application | (6.25 mg/mL/ 6.25 mg/mL) in THF/H₂O (80/20) | None | 3 |
| 7-B | One application | (6.25 mg/mL/ 6.25 mg/mL) in THF/H₂O (80/20) | THF/H₂O (92/8) One application | 2 |
| 7-C | One application | None | THF/H₂O (92/8) One application | 3 |
| 7-D | Two applications | None | THF/H₂O (92/8) Two applications | 3 |

Results showed that premixing the heparin with PLA did not improve bonding of the heparin with the substrate (stents containing PLA on their surfaces). Moreover, multiple applications of the PLA/Compound IV premix did not improve heparin binding.

Example 8

The effect of spray coating with simultaneous illumination was observed as follows. Stents having a coating of PLA/rapalog were spray coated with photo-heparin in water (various applications of spray coat, as indicated below; for stents with multiple coatings, the stent was rinsed with diH₂O, blown with nitrogen gas, then air dried for at least 5 minutes after each application). During spray coating, the stents were illuminated with light through an Edmund 407 nm filter (with the exception of Sample No. 8-D, for which no filter was used), with various UV intensity (indicated below). For Sample 8-E, an outer coat of photo-heparin was sprayed onto the stents after the stents were allowed to air dry. For this sample, the stents were illuminated after the outer coating was applied.

Results showed that increased UV intensity improves the binding of the heparin to the substrate. Therefore, if it is desired to eliminate use of a filter during binding of the heparin, one could utilize a higher UV intensity instead. Results also showed that utilization of an outer coat of photo-heparin did not improve heparin binding as compared to the other samples of this set.

Example 9

The effect of utilizing crosslinking agents or a photoreactive polymer in a coating, the coating also including photo-heparin, was observed as follows. Stents having a coated layer of pLA/rapalog as described in Example 2 were used as substrates. -

Various compositions were prepared and coated on the PLA/rapalog layer. These compositions included the following:

Non-water soluble photo-crosslinking agent (TBBE; Compound I)

Mixture of water soluble photo-crosslinking agent and photo-heparin

Mixture of water soluble photo-crosslinking agent, photo-heparin, and PLA

Mixture of water soluble photo-crosslinking agent and PLA

Water soluble photo-crosslinking agent (DBDS; Compound II)

Water soluble photo-crosslinking agent (TEMED-DQ; Compound III)

After these compositions were coated, a photo-heparin composition was coated on these.

Pre-mixtures containing a crosslinking agent having photoreactive groups, or a photoreactive polymer (various, as indicated below) were prepared. The premix was spray coated onto the stents. Some of the stents were illuminated with light, as indicated below (Edmund 407 nm filter, 1-1.3 mW/cm², seconds). For other stents, an outer coating of Compound IV was spray coated onto the stents, followed by illumination with UV having an intensity of 1-1.3 mW/cm for 60 seconds, utilizing an Edmund 407 nm filter. For all outer coat compositions, concentration of Compound IV was 4 mg/mL in THF/H₂O (92/8) followed by illumination (Edmund 407 nm filter, 1-1.3 mW/cm², seconds).

TABLE 8

| Sample No. | Photo-heparain spray coating | UV intensity during spray | Flow rate during spray coating | Photo-heparin Outer coating | Heparin activity (mU/cm²) |
|---|---|---|---|---|---|
| 8-A | One application | 0.5 mW/cm² | 0.1 mL/min | None | 5 |
| 8-B | One application | 0.5 mW/cm² | 0.2 mL/min | None | 5 |
| 8-C | Three applications | 0.5 mW/cm² | 0.1 mL/min | None | 5 |
| 8-D | One application | >20 mW/cm² | 0.1 mL/min | None | 11 |
| 8-E | One application | 0.5 mW/cm² during spray; 1-1.3 mW/cm² after spray of outer coating | 0.1 mL/min | Compound IV | 3 |

TABLE 9

| Sample No. | Premix (concentration) sprayed on for 1-4 Immersed 5-7 | Illumination stages | Heparin activity (mU/cm$^2$) |
|---|---|---|---|
| 9-A | TBBE (2.3 mg/mL in THF) Spray coated | Post spray, post outer coat | 56 |
| 9-B | TBBE/photo-heparin (1.67/6.25 mg/mL) in THF/H$_2$O (87.5/12.5) Spray coated | Post spray, post outer coat | >57 |
| 9-C | PLA/TBBE/photo-heparin (5/1.67/6.25 mg/mL) in THF/H$_2$O (87.5/12.5) Spray coated | Post spray, post outer coat | 40 |
| 9-D | PLA/TBBE (5/3.3) in THF Spray coated | Post spray, post outer coat | >57 |
| 9-E | DBDS (5 mg/mL) in H$_2$O Immersion coated | In-solution and post outer coat spray | 23 |
| 9-F | DBDS (5 mg/mL) in H$_2$O Immersion coated | In-solution and post outer coat spray | 15 |
| 9-G | TEMED-DQ (1 mg/mL) in H$_2$O Immersion coated | In-solution and post outer coat spray | 22 |

Results indicated that improved heparin binding can be achieved by utilizing crosslinking agents and/or by preparing premixes as described above.

We claim:

1. A medical article having a bioactive agent-releasing coating having heparin activity of 10 mU/cm$^2$ or greater, the coating comprising:
   (a) a first coated layer comprising bio-stable or biodegradable polymer and bioactive agent; and
   (b) a second coated layer comprising heparin and photoreactive groups.

2. The medical article of claim 1 wherein the bioactive agent-releasing coating has heparin activity of 20 mU/cm$^2$ or greater.

3. The medical article of claim 1 wherein the bioactive agent is selected from macrolide antibiotics, immunomodulatory agents, and anti-mitotics.

4. The medical article of claim 2 wherein the macrolide antibiotic is selected from the group of consisting of rapamycin, tacrolimus, ABT-578, and everolimus.

5. The medical article of claim 1 comprising a bio-stable polymer that is a vinyl polymer.

6. The medical article of claim 5 wherein the vinyl polymer is an ethylene vinyl alcohol copolymer.

7. The medical article of claim 1 comprising a biodegradable polymer that is selected from polylactic acid, polyglycolic acid, and copolymers thereof.

8. The medical article of claim 1 wherein heparin comprises pendent photoreactive groups.

9. The medical article of claim 1 further comprising a component selected from the group of non-water soluble crosslinking agents, vinylpyrrolidone polymers, polyethylene glycol, polyethylene glycol sulfonates, fatty quaternary amines, fatty sulfonates, fatty acids, dextran, dextran, dextrin, and cyclodextrin, the component having pendent photo-reactive groups.

10. The medical article of claim 9 wherein the component comprises vinylpyrrolidone polymers having pendent photoreactive groups.

11. The medical article of claim 9 wherein the component comprises a non-water soluble crosslinking agent having two or more pendent photoreactive groups.

12. The medical article of claim 1 being an intraluminal prosthesis.

13. The medical article of claim 12 being a stent.

14. A medical article having a coating with heparin activity, the coating comprising:
   (a) a first coated layer comprising polymer and bioactive agent, wherein the bioactive agent maximally absorbs light at a wavelength of below 300 nm; and
   (b) a second coated layer comprising heparin and photoreactive groups, wherein the photoreactive groups maximally absorb light at a wavelength of 320 nm or above, wherein the second coated layer is formed by applying irradiation through a filter in an amount in the range of 0.12 J/cm2 to 0.96 J/cm2 as measured at 335 nm, and wherein the filter is selected from the group consisting of from ultra-violet cut-off filters, ultra-violet transmitting filters, band pass filters, and colored filters.

15. A medical article having a coating with heparin activity, the coating comprising:
   (a) a first coated layer comprising a polymer selected from vinyl polymers, and a bioactive agent; and
   (b) a second coated layer comprising heparin and photoreactive groups.

16. A medical article having a biodegradable coating with heparin activity, the coating comprising:
   (a) biodegradable polymer;
   (b) bioactive agent;
   (c) heparin having pendent photo-reactive groups; and
   (d) a component selected from the group of non-water soluble crosslinking agents, vinylpyrrolidone polymers, polyethylene glycol, polyethylene glycol sulfonates, fatty quaternary amines, fatty sulfonates, fatty acids, dextran, dextrin, and cyclodextrin, the component having pendent photo-reactive groups.

17. The medical article of claim 1 wherein the bio-stable or biodegradable polymer is soluble in chloroform.

\* \* \* \* \*